(12) United States Patent
Tobias et al.

(10) Patent No.: US 10,532,132 B2
(45) Date of Patent: *Jan. 14, 2020

(54) IMPLANTABLE DRUG DELIVERY DEVICE AND METHODS

(71) Applicants: Irene Sophie Tobias, Cambridge, MA (US); Heejin Lee, Arlington, MA (US); Michael J. Cima, Winchester, MA (US); Jordan Dimitrakov, Boston, MA (US)

(72) Inventors: Irene Sophie Tobias, Cambridge, MA (US); Heejin Lee, Arlington, MA (US); Michael J. Cima, Winchester, MA (US); Jordan Dimitrakov, Boston, MA (US)

(73) Assignees: CHILDREN'S MEDICAL CENTER CORPORATION, Boston, MA (US); MASSACHUSETTS INSTITUTE OF TECHNOLOGY, Cambridge, MA (US)

(*) Notice: Subject to any disclaimer, the term of this patent is extended or adjusted under 35 U.S.C. 154(b) by 1443 days.

This patent is subject to a terminal disclaimer.

(21) Appl. No.: 13/910,730

(22) Filed: Jun. 5, 2013

(65) Prior Publication Data

US 2013/0324946 A1  Dec. 5, 2013

Related U.S. Application Data

(60) Division of application No. 12/538,580, filed on Aug. 10, 2009, now abandoned, which is a continuation-in-part of application No. 11/463,956, filed on Aug. 11, 2006, now Pat. No. 8,801,694.

(60) Provisional application No. 60/726,490, filed on Oct. 12, 2005, provisional application No. 60/707,676, filed on Aug. 11, 2005, provisional application No. 61/087,687, filed on Aug. 9, 2008.

(51) Int. Cl.
*A61L 31/06* (2006.01)
*A61L 31/16* (2006.01)

(52) U.S. Cl.
CPC .............. *A61L 31/06* (2013.01); *A61L 31/16* (2013.01)

(58) Field of Classification Search
None
See application file for complete search history.

(56) References Cited

U.S. PATENT DOCUMENTS

| | | |
|---|---|---|
| 3,854,480 A | 12/1974 | Zaffaroni |
| 3,888,975 A | 6/1975 | Ramwell |
| 3,901,232 A | 8/1975 | Michaels et al. |
| 3,935,860 A | 2/1976 | Hoff |
| 4,016,251 A | 4/1977 | Higuchi et al. |
| 4,235,236 A | 11/1980 | Theeuwes |
| 4,392,848 A | 7/1983 | Lucas et al. |
| 4,449,980 A | 5/1984 | Millar et al. |
| 4,475,916 A | 10/1984 | Himmelstein |
| 4,629,449 A | 12/1986 | Wong |
| 4,655,219 A | 4/1987 | Petruzzi |
| 4,678,463 A | 7/1987 | Millar |
| 4,871,542 A | 10/1989 | Vilhardt |
| 4,968,507 A | 11/1990 | Zentner et al. |
| 5,366,738 A | 11/1994 | Rork et al. |
| 5,441,550 A | 8/1995 | Hassenboehler, Jr. et al. |
| 5,499,997 A | 3/1996 | Sharpe et al. |
| 5,516,522 A | 5/1996 | Peyman et al. |
| 5,551,954 A | 9/1996 | Buscemi et al. |
| 5,709,874 A | 1/1998 | Hanson et al. |
| 5,788,980 A | 8/1998 | Nabahi |
| 5,795,591 A | 8/1998 | Lee et al. |
| 5,797,898 A | 8/1998 | Santini, Jr. et al. |
| 5,830,230 A | 11/1998 | Berryman et al. |
| 5,851,217 A | 12/1998 | Wolff et al. |
| 5,855,906 A | 1/1999 | McClay |
| 5,869,081 A | 2/1999 | Jackanicz et al. |
| 5,972,372 A | 10/1999 | Saleh et al. |
| 5,989,581 A | 11/1999 | Groenewegen |
| 6,039,967 A * | 3/2000 | Ottoboni .............. A61K 9/0034 424/426 |

(Continued)

FOREIGN PATENT DOCUMENTS

| | | |
|---|---|---|
| DE | 3332156 A1 | 3/1985 |
| EP | 0572932 A2 | 12/1993 |

(Continued)

OTHER PUBLICATIONS

Collins et al., How Common is Prostatitis? A National Survey of Physician Visits. Journal of Urology, 159(4); 1224-1228 (1998).

(Continued)

*Primary Examiner* — Melissa L Fisher

(74) *Attorney, Agent, or Firm* — Eversheds Sutherland (US) LLP

(57) ABSTRACT

A method is provided for local controlled delivery of a drug to the seminal vesicle, the prostate, the ejaculatory duct, or the vas deferens of a patient in need of treatment. In one embodiment, the method includes implanting a resorbable drug delivery device within the seminal vesicle, the prostate, the ejaculatory duct, or the vas deferens of the patient. The drug delivery device may include an elastic device body housing at least one drug reservoir which contains at least one drug. In a preferred embodiment, the method further includes releasing the drug from the device in a controlled manner to, typically directly to, the seminal vesicle, the prostate, the ejaculatory duct, or the vas deferens.

15 Claims, 15 Drawing Sheets

(56) References Cited

U.S. PATENT DOCUMENTS

| | | | |
|---|---|---|---|
| 6,039,968 A | 3/2000 | Nabahi | |
| 6,083,933 A | 7/2000 | Hahn | |
| 6,086,909 A | 7/2000 | Harrison et al. | |
| 6,139,535 A | 10/2000 | Greelis et al. | |
| 6,171,298 B1* | 1/2001 | Matsuura | A61L 17/145 604/246 |
| 6,207,180 B1 | 3/2001 | Ottoboni et al. | |
| 6,293,923 B1 | 9/2001 | Yachia et al. | |
| 6,398,718 B1 | 6/2002 | Yachia et al. | |
| 6,416,780 B1 | 7/2002 | Passmore et al. | |
| 6,444,224 B1 | 9/2002 | Rathbone et al. | |
| 6,464,999 B1 | 10/2002 | Huo et al. | |
| 6,482,837 B1 | 11/2002 | Wood | |
| 6,491,666 B1 | 12/2002 | Santini, Jr. et al. | |
| 6,524,608 B2 | 2/2003 | Ottoboni et al. | |
| 6,682,473 B1 | 1/2004 | Matsuura et al. | |
| 6,712,784 B2 | 3/2004 | Huang | |
| 6,746,421 B2 | 6/2004 | Yachia et al. | |
| 6,749,617 B1 | 6/2004 | Palasis et al. | |
| 6,753,011 B2 | 6/2004 | Faour | |
| 6,808,522 B2 | 10/2004 | Richards et al. | |
| 6,899,890 B2 | 5/2005 | Kirschner et al. | |
| 6,932,810 B2 | 8/2005 | Ryan | |
| 6,951,654 B2 | 10/2005 | Malcolm et al. | |
| 6,973,718 B2 | 12/2005 | Sheppard et al. | |
| 6,976,950 B2 | 12/2005 | Connors et al. | |
| 6,976,951 B2 | 12/2005 | Connors et al. | |
| 6,988,983 B2 | 1/2006 | Connors et al. | |
| 7,005,138 B2 | 2/2006 | Mahashabde et al. | |
| 7,074,178 B2 | 7/2006 | Connors et al. | |
| 7,521,064 B2 | 4/2009 | Saxena et al. | |
| 7,647,112 B2 | 1/2010 | Tracey et al. | |
| 2002/0164374 A1 | 11/2002 | Jackson et al. | |
| 2003/0059456 A1 | 3/2003 | Malcolm et al. | |
| 2003/0118649 A1 | 6/2003 | Gao et al. | |
| 2003/0118692 A1 | 6/2003 | Wang et al. | |
| 2003/0139800 A1 | 7/2003 | Campbell | |
| 2003/0147936 A1 | 8/2003 | Sahadevan | |
| 2003/0229263 A1 | 12/2003 | Connors et al. | |
| 2004/0013702 A1 | 1/2004 | Glover | |
| 2004/0022824 A1 | 2/2004 | Li et al. | |
| 2004/0034332 A1 | 2/2004 | Uhland | |
| 2004/0220552 A1 | 11/2004 | Heruth et al. | |
| 2004/0260272 A1 | 12/2004 | Friedman et al. | |
| 2005/0228482 A1 | 10/2005 | Herzog et al. | |
| 2005/0234013 A1 | 10/2005 | Parsons et al. | |
| 2005/0234431 A1 | 10/2005 | Williams et al. | |
| 2005/0238733 A1 | 10/2005 | Henry | |
| 2006/0105010 A1 | 5/2006 | Rahe et al. | |
| 2006/0234978 A1 | 10/2006 | Marcum | |
| 2006/0259118 A1 | 11/2006 | Pal et al. | |
| 2006/0264897 A1 | 11/2006 | Lobl et al. | |
| 2006/0264912 A1 | 11/2006 | McIntyre et al. | |
| 2007/0172507 A1 | 7/2007 | Zupkas et al. | |
| 2007/0172508 A1 | 7/2007 | Zupkas et al. | |
| 2007/0196423 A1* | 8/2007 | Ruane | A61L 31/10 424/423 |
| 2007/0202151 A1 | 8/2007 | Lee et al. | |
| 2007/0254014 A1 | 11/2007 | Ahmed et al. | |
| 2008/0051740 A1 | 2/2008 | Sokal et al. | |
| 2009/0004246 A1 | 1/2009 | Woolfson et al. | |
| 2009/0149833 A1 | 6/2009 | Cima et al. | |
| 2010/0076261 A1 | 3/2010 | Neeman et al. | |

FOREIGN PATENT DOCUMENTS

| | | | |
|---|---|---|---|
| WO | 9918884 A1 | 4/1999 | |
| WO | 0040234 A1 | 7/2000 | |
| WO | 02085428 A2 | 10/2002 | |
| WO | 03009882 A2 | 2/2003 | |
| WO | 04037318 A2 | 5/2004 | |
| WO | 2005032524 A2 | 4/2005 | |
| WO | 05072751 A1 | 8/2005 | |
| WO | 05115245 A1 | 12/2005 | |
| WO | 06121969 A1 | 11/2006 | |
| WO | 07115259 A2 | 10/2007 | |
| WO | 2008038281 A2 | 4/2008 | |
| WO | 08115536 A2 | 9/2008 | |
| WO | 09029958 A2 | 3/2009 | |

OTHER PUBLICATIONS

Grayson et al., Multi-pulse Drug Delivery from a Resorbable Polymeric Microchip Device, Nat. Mater 2(11); 1-6 (2003).

Grayson et al. Molecular Release from a Polymeric Microreservoir Device: Influence of Chemistry, Polymer Swelling, and Loading on Device Performance,. J. Biomed Mat Res 69A(3); 502-512 (2004).

Santus et al, Osmotic Drug Delivery: A Review of the Patent Literature, Journal of Controlled Release 35; 1-21 (1995).

Theeuwes, Elementary Osmotic Pump. Journal of Pharm Sci 64(12); 1987-91 (1975).

Wright et al. Duros Osmotic Pharmaceutical Systems for Parenteral & Site-Directed Therapy. Drug Delivery Technology 3(1) 2003.

Wright & Stevenson, Pumps/Osmotic, Encyclopedia of Controlled Drug Delivery, vol. 2, New York; John Wiley (1999) pp. 896-920.

Beiko, Urinary Tract Biomaterials, Journal of Urology, vol. 171, 2438-2444, (2004).

Au et al., Methods to Improve Efficacy of Intravesical Mitomycin C: Results of a Randomized Phase III Trial, Journal of National Cancer Institute, Apr. 18, 2001, 597-604, vol. 93-98, Oxford University Press.

Carr et al.. Evaluation of a Transoral Delivery System for Topical Anesthesia, The Journal of the American Dental Association, Dec. 2001, 1714-1719, vol. 132, American Dental Association.

Dentipatch (lidocaine) Patch [Noven Parmaceuticals, Inc.], downloaded from http://dailymed.nlm.nih.gov/dailymed/fdaDrugXsl.cfm?id=1543&type=display on Feb. 22, 2007.

Gammaitoni et al., Safety and Tolerability of the Lidocaine Patch 5%, a Targeted Peripheral Analgesic: A Review of the Literature, The Journal of Clinical Pharmacology, 2003, 111-117, vol. 43, American College of Clinical Pharmacology.

Gasion et al., Improving Efficacy of Intravesical Chemotherapy, European Urology, 2006, 225-234, vol. 50, Elsevier B.V.

Giannantoni et al., New Frontiers in Intravesical Therapies and Drug Delivery, European Urology, 2006, 1183-1193, vol. 50, ElsevierB.V.

Highley et al., Intravesical Drug Delivery Pharmacokinetic and Clinical Considerations, Clinical Pharmacokinet, Jul. 1999, 59-73, vol. 37 (1), Adis International Limited.

Malmstrom, Intravesical Therapy of Superficial Bladder Cancer, Critical Reviews in Oncology Hematology, 2003, 109-126, vol. 47, Elsevier Science Ireland Ltd.

Tyagi, et al., Local Drug Delivery to Bladder Using Technology Innovations, Urological Clinics of North America, 2006, 519-530, vol. 33, Elsevier Inc.

Walker et al., Intravesical Chemotherapy: In Vitro Studies on the Relationship Between Dose and Cytotoxicity, Urological Research, 1986, 137-140, vol. 14, Springer-Verlag.

Verma, et al., Formulation Aspects in the Development of Osmotically Controlled Oral Drug Delivery Systems, Journal of Controlled Released, 2002, 7-27, vol. 79, Elsevier Science B.V.

Li et al., Water Based Silicone Elastomer Controlled Release Tablet Film Coating III-Drug Release Mechanisms, Drug Development and Industrial Pharmacy, 1989, 1943-1968, vol. 15(12), Marcel Dekker, Inc.

Thombre et al., Mechanism of Water Transport in Controlled Porosity Osmotic Devices, Journal of Membrane Science, 1989, 279-310, vol. 40, Elsevier Science Publishers B.V.

Stymne et al., Plasma Concentrations of Lignocaine and Prilocaine after a 24-h Application of Analgesic Cream (EMLA®) to Leg Ulcers, British Journal of Dermatology, 2001, 530-534, vol. 145, British Association of Dermatologists.

http://www.ic-network.com/handbooklinstill.html, last updated Mar. 16, 2006.

(56) References Cited

OTHER PUBLICATIONS

Kim et al., Antimuscarinic Agents Exhibit Local Inhibitory Effects on Muscarinic Receptors in Bladder-Afferent Pathways, 2005, 238-242, Elsevier Inc.

Vassileva et al., Novel Biocompatible Intraperitoneal Drug Delivery System Increases Tolerability and Therapeutic Efficacy of Paclitaxel in a Human Ovarian Cancer Xenograft Model, Cancer Chemother Pharmacal, 2007, 60:907-914, Springer-Verlag.

Sprati et al., Clinical Delivery System for Intraperitoneal Hyperthermic Chemotherapy, Cancer Research, Feb. 1980 40:256-260.

Morimoto et al., Management of Patients with Recurrent Nephrosis and Intractable Edema by Intraperitoneal Instillation of Icodextrin Solution, Peritoneal Dialysis International, Sep. 2008, vol. 28, No. 5, 559-561.

Larsson, et al., Effect of Intraperitoneal Instillation of 32% Dextran 70 on Postoperative Adhesion Formation After Tubal Surgery, 1985, Acta Obstet Gynecol Scand 64:437-441.

Jiranantarat et al., Analgesic Effect of Intraperitoneal Instillation of Bupivacaine for Postoperative Laparoscopic Cholecystectomy, J. Med Assoc Thai, Sep. 2002, 85 (Suppl 3): S897-S903.

All, et al., Lidocaine as Endotracheal Tube Cuff Inflating Agent, JAFMC Bangladesh, Jun. 2009, pp. 25-28, vol. 5, No. 1.

Dollo, et al., Endotracheal Tube Cuffs Filled With Lidocaine as a Drug Delivery System in Vitro and in Vivo Investigations, European Journal of Pharmaceutical Sciences, 2001, pp. 319-323, vol. 13, Elsevier Sciences B.V.

Estebe, et al., Alkalinization of Intra-Cuff Lidocaine and Use of Gel Lubrication Protect Against Tracheal Tube-Induced Emergence Phenomena, British Journal of Anasthesia, 2004, pp. 361-366, vol. 92, No. 3, The Board of Management and Trustees of the British Journal of Anasthesia.

Estebe, et al., Alkalinization of Intracuff Lidocaine Improves Endotracheal Tube-Induced Emergence Phenomena, Anesth Analg, 2002, pp. 227-230, vol. 94, International Anesthesia Research Society.

Estebe, et al., Alkalinization of Intracuff Lidocaine: Efficacy and Safety, Anesth Analg, 2005, pp. 1536-1541, vol. 101, International Anesthesia Research Society.

Russell, et al., High-performance Liquid Chromatographic Determination of 17-Estradiol and 17-Estradiol-3-Acetate Solubilities and Diffusion Coefficients in Silicone Elastomeric Intravaginal Rings, Journal of Chromatography B, 2000, pp. 157-163, vol. 744, Elsevier Science, B.V.

Sconzo, M.D., et al., In Vitro Diffusion of Lidocaine Across Endotracheal Tube Cuffs, Regional Anesthesia, Jan.-Feb. 1990, pp. 37-40.

Woolfson, et al., Design of a Silicone Reservoir Intravaginal Ring for the Delivery of Oxybutynin, Journal of Controlled Release, 2003, pp. 465-476, vol. 91, Elsevier B.V.

Woolfson. et al., Design of an Intravaginal Ring for the Controlled Delivery of 17-Estradiol as its 3-Acetate Ester, Journal of Controlled Release, 1999, pp. 319-328, vol. 61, Elsevier Science B.V.

\* cited by examiner

IMPLANTABLE DRUG DELIVERY DEVICE AND METHODS

CROSS-REFERENCE TO RELATED APPLICATIONS

This application is a divisional of U.S. application Ser. No. 12/538,580, filed Aug. 10, 2009, which is a continuation-in-part of U.S. application Ser. No. 11/463,956, filed Aug. 11, 2006. Priority benefit is also claimed to U.S. Provisional Application No. 60/726,490, filed Oct. 12, 2005; U.S. Provisional Application No. 60/707,676, filed Aug. 11, 2005; and U.S. Provisional Application No. 61/087,687, filed Aug. 9, 2008. All of these applications are incorporated herein by reference in their entirety.

BACKGROUND OF THE INVENTION

This invention is generally in the field of medical devices, and more particularly relates to implantable drug delivery devices for controlled release of drug locally to a tissue site.

The efficacy of many drugs is directly related to the way in which they are administered. Various systemic methods of drug delivery include oral, intravenous, intramuscular, and transdermal. These systemic methods may produce undesirable side effects and may result in the metabolization of the drug by physiological processes, ultimately reducing the quantity of drug to reach the desired site. Accordingly, a variety of devices and methods have been proposed to deliver drug in a more targeted manner, such as locally, to address many of the problems associated with systemic drug delivery.

Prostatitis is an inflammatory condition of the prostate gland. Typically, prostatitis is a painful disorder that presents with symptoms that often include chronic pelvic pain, urinary dysfunction (in the form of frequency, urgency or weak stream, pain on urination) and sexual dysfunction. The condition is estimated to be prevalent among 10% of all men and is believed to be symptomatic in half the male population at some point in their lifetime. Prostatitis can occur either as an acute infection of the prostate gland, known as acute bacterial prostatitis, or more commonly as a recurring condition, known as chronic prostatitis.

Chronic prostatitis is characterized as being bacterial (CBP) or abacterial (ACP) based on the isolation of a suspected causative pathogen from the prostatic fluid or urine. Bacteria are believed to cause a significant percentage of chronic prostatitis cases, such as 5 to 15% of such cases. Current recommendations provide that all patients presenting with chronic prostatitis (both CBP and ACP) should be treated initially with antibiotics for 2 weeks and should receive continued treatment if symptoms improve. The choice of antibiotic can be critical, as the prostate and nearby seminal vesicles present a significant pH gradient. Thus, the chosen antibiotic should have sufficient chemical stability over a range of pH (e.g., 7.2 to 8.0) while also exhibiting effective penetration into the prostate gland. The zwitterionic fluoroquinolones such as ciprofloxacin (CIP) and levofloxacin have surpassed older drug treatments for chronic prostatitis such as trimethoprin-sulfamethoxazole (TMP-SMZ) in both effective bacterial eradication and cost-effectiveness. A 500 mg dose of CIP administered twice a day for 28 days yielded bacteriological cure rates of 63-76% in clinical studies, whereas most studies on TMP-SMZ or TMP alone yielded efficacy rates between 30-50% and required longer duration of therapy, such as 90 days. Significant room therefore still exists for improvement in the cure rate.

Some have advocated direct injection of antibiotics to the prostate gland due to the relatively high failure rate of systemic antibiotic administration. The failure of oral antibiotics is mainly thought to be due to an associated local autoimmune disease process and the possible presence of intraprostatic bacterial biofilms which resist drug penetration, providing a therapeutic argument for local antibiotic administration. Guercini et al. (*Arch Ital Urol Androl* 77:87-92 (2005)) have also demonstrated enhanced improvement in therapy with additional co-administration of betamethasone, an immuno-suppressing steroid infused in a cocktail solution with antibiotics, to the prostate in order to counter the effects of the autoimmune disease process. In that study, chronic prostatitis patients who had experienced repeated failure of oral antibiotics in the previous 12 months underwent prostatic infiltration of antibiotics and betamethasone. In the study, 68% of the study participants were effectively cured, and 13% of the participants showed no response. While local prostate antibiotic injection has shown reasonable efficacy in clinical trials, it has not yet become a popular or widespread therapy in use among most urologists.

The seminal vesicles are a pair of coiled tubular glands which form lateral outpouchings of the ampulla of the vas deferens, which connects the epididymis of the testes to the prostate gland. The seminal vesicles and the ampulla form the ejaculatory duct which empties into the prostate gland. Infection and inflammation of the seminal vesicles (vesiculitis) is uncommon in the United States, and it is usually treated with systemic antibiotics. Cancer originating in the seminal vesicles is rare, although secondary invasion of tumors from the nearby prostate gland, bladder, or rectum is more common. One identified brachytherapy treatment for prostate cancer with secondary seminal vesicle involvement includes the implantation of radioactive $^{103}$Pd seeds.

Accordingly, a need exists to provide a local drug delivery device and method to replace multiple intraprostatic injections as a sustained treatment of antibiotics over an extended period. In addition, it would be desirable to provide alternatives for treating vesiculitis, cancer, or other diseases and conditions involving the seminal vesicles, ampulla, prostate, and/or surrounding tissues, particularly in a minimally invasive manner for local delivery of one or more drugs.

It would be further desirable to provide treatments in which a therapeutically effective amount of drug can be administered over an extended period to one or more urological tissue sites without a strict or complicated dosing regimen. In addition, there is a need for controlled drug device that is suitable for delivery into and retention in a genitourinary site in a patient, such as a seminal vesicle, vas deferens, ejaculatory duct, or prostate. In particular, there is a need for materials of construction that are functional for storing and releasing drug, that are suitably elastic for minimally invasive deployment and retention, and that do not require explantation following completion of the drug release.

SUMMARY OF THE INVENTION

In one aspect, a method is provided for local controlled delivery of a drug to the seminal vesicle, the prostate, the ejaculatory duct, or the vas deferens of a patient in need of treatment. In one embodiment, the method includes implanting a resorbable drug delivery device within the seminal vesicle, the prostate, the ejaculatory duct, or the vas deferens of the patient. The drug delivery device may include an elastic device body housing at least one drug reservoir which contains at least one drug. In a preferred embodiment, the method further includes releasing the drug (i.e., permitting the drug to be released) from the device in a controlled manner to, typically directly to, the seminal vesicle, the prostate, the ejaculatory duct, or the vas deferens.

In one embodiment, the step of implanting the resorbable drug delivery device includes placement of a catheter in the urethra followed by cystoscopic deployment of the drug delivery device through the catheter. In another embodiment, the step of implanting the resorbable drug delivery device includes transrectal injection. In various embodiments, the step of implanting the drug delivery device further includes imaging and positioning of the drug delivery device by transrectal ultrasonography.

In various applications of the device and methods described herein, the patient may present with chronic prostatitis, vesiculitis, post-prostatectomy complications, or a cancer involving the prostate gland, bladder, or rectum.

In certain embodiments, the device body includes an elastomeric poly(glycerol-sebacic acid). In various embodiments, the release of the drug in vivo is osmotically driven for at least a majority of the drug payload that is released. In a particular embodiment, the device body degrades by surface erosion into biocompatible monomers, following release of substantially all of the drug from the device body.

In one embodiment, a method is provided for local delivery of a drug to a genitourinary tissue site of a patient in need of treatment that includes implanting a resorbable drug delivery device within a tissue lumen at a genitourinary site of the patient. In an alternative embodiment, implantation of the resorbable drug delivery device is within a non-lumenal genitourinary tissue site of the patient. The drug delivery device may include an elastic device body housing at least one drug reservoir which contains at least one drug. The step of implantation may include insertion of the device through a bore of a hollow needle or cannula. The method also includes permitting the drug to be released from the device in a controlled manner to the genitourinary site.

In another aspect, a method is provided for making an implantable drug delivery device. The method includes providing a pre-polymer for forming a biocompatible, resorbable elastomer; extruding or molding the pre-polymer into a device body having an elongated shape which comprises a first end, an opposed second end, at least one sidewall between the first and second ends and a hollow bore defined by the at least one sidewall; polymerizing the pre-polymer to produce a cross-linked elastomeric polymer; loading a drug formulation into the hollow bore; and closing off the hollow bore at positions to contain the drug formulation therein to form an implantable drug delivery device, which is dimensioned and has an elasticity suitable for deployment of the drug delivery device via urethral catheterization or transrectal injection into and retention in a genitourinary site in a patient.

In another aspect, an implantable medical device is provided that includes a resorbable, elastic device body having at least one elongated sidewall and at least one payload reservoir defined therein. The device body provides in vivo controlled release of a payload which may be stored in the payload reservoir. The implantable medical device is dimensioned and has an elasticity suitable for deployment of the medical device via urethral catheter or transrectal injection into and retention in a genitourinary site in a patient. In certain embodiments, the device is dimensioned and has an elasticity suitable for deployment into and retention in a seminal vesicle, ejaculatory duct, prostate, or vas deferens in a patient.

In various embodiments, the resorbable, elastic device body includes an elastomeric polymer. In some embodiments, the elastomeric polymer is a hydrophobic elastomeric polyester, such as a poly(glycerol-sebacic acid). In some embodiments, the elastomeric polymer includes a poly(caprolactone), a polyanhydride, an amino alcohol-based poly(ester amide), or a poly(octane-diol citrate).

In various embodiments, the device may provide controlled release of the payload in vivo by osmotic pump action, diffusion, surface erosion of the device body or a part thereof, or a combination of these mechanisms.

The device body may include one or more apertures. In some such embodiments, the sidewalls are selectively permeable to water and essentially impermeable to the payload. In further such embodiments, release of the payload from the device in vivo is osmotically driven. In some embodiments, the diameter of each of the one or more apertures is between about 20 and about 300 µm. In further such embodiments, the device includes a degradable membrane in register with at least one of the one or more apertures. For example, release of payload from the reservoir through the aperture is delayed until the membrane has degraded in vivo. Degradation of the membrane in vivo would occur, in a typical embodiment, before degradation of the device body in vivo.

In one embodiment, release of the payload from the device in vivo occurs by diffusion through one or more apertures in the device body, the sidewall of the device body, or a combination thereof. In another embodiment, release of the payload from the device in vivo occurs by surface erosion of the device body. In one case, such an erodible device body may comprise an erodible matrix material with at least one drug, which may be dispersed in the matrix material.

In preferred embodiments, the payload includes at least one drug. In various embodiments, the drug includes an antibiotic agent, an immunosuppressant, an anti-inflammatory agent, a chemotherapeutic agent, a local anesthetic, or a combination thereof. In a preferred embodiment, the drug in the payload reservoir is in a solid form or semi-solid form.

In a certain embodiment, the device is sized and shaped to fit into a 14 to 18 gauge transrectal needle. In another certain embodiment, the device is sized and shaped to fit into a 16 to 18 French urethral catheter. In another embodiment, the device is configured to be passed through a catheter and is capable of being urged through the catheter by a stylet.

In certain embodiments, the device body has an outer diameter between about 0.6 mm and about 3 mm. In one embodiment, the device body has a length between about 1 cm and about 7 cm. In one embodiment, the sidewalls have a thickness between about 100 µm and about 600 µm.

In one embodiment, the device body includes two or more discrete payload reservoirs. These may be defined by the sidewalls and at least one partition.

In one embodiment, an implantable drug delivery device is provided that includes a resorbable, elastic device body having at least one elongated sidewall, at least one drug reservoir defined therein, and at least one drug formulation in the drug reservoir. The device body may include a hydrophobic elastomeric polyester which degrades in vivo by surface erosion. The device body preferably provides controlled release of the drug in vivo. In a preferred embodiment, the implantable drug delivery device is dimensioned and has an elasticity suitable for deployment of the drug delivery device via urethral catheter or transrectal injection into and retention in a seminal vesicle, prostate, ejaculatory duct, or vas deferens in a patient. In one embodiment, the hydrophobic elastomeric polyester comprises or consists of a poly(glycerol-sebacic acid). In a preferred embodiment, the device body includes at least one aperture and provides controlled release of the drug in vivo by osmotic pressure.

An osmotic pump device may include a housing and a drug contained in the housing. The housing may be made of a bioresorbable elastomer and may have at least one aperture. The pump device may be configured to dispense the drug in vivo, driven by osmotic pressure, through the at least one aperture. In particular embodiments, the bioresorbable elastomer comprises a poly(glycerol-sebacic acid). In a preferred embodiment, the osmotic pump device is dimensioned and has an elasticity suitable for deployment into and retention in a seminal vesicle, prostate, ejaculatory duct, or vas deferens in a patient.

DETAILED DESCRIPTION OF THE INVENTION

Devices and methods have been developed for delivery of a drug to one or more sites of the male genitourinary system, such as the seminal vesicle, the prostate gland, the vas deferens, or the ejaculatory duct. In one embodiment, a device is wholly implanted in a portion of the male genitourinary system to provide drug delivery at the implantation site and surrounding tissues, particularly over an extended period of time, for example a time period of about two days to about four weeks. For example, the device may be dimensioned and may have an elasticity suitable for deployment of the medical device via urethral catheterization or transrectal injection into and retention in a genitourinary site, such as a seminal vesicle, ejaculatory duct, or ampulla in a patient. The device may release one or more drugs. For example, the device may provide controlled release of the drug in vivo, such as by osmotic pressure.

Figure 1:
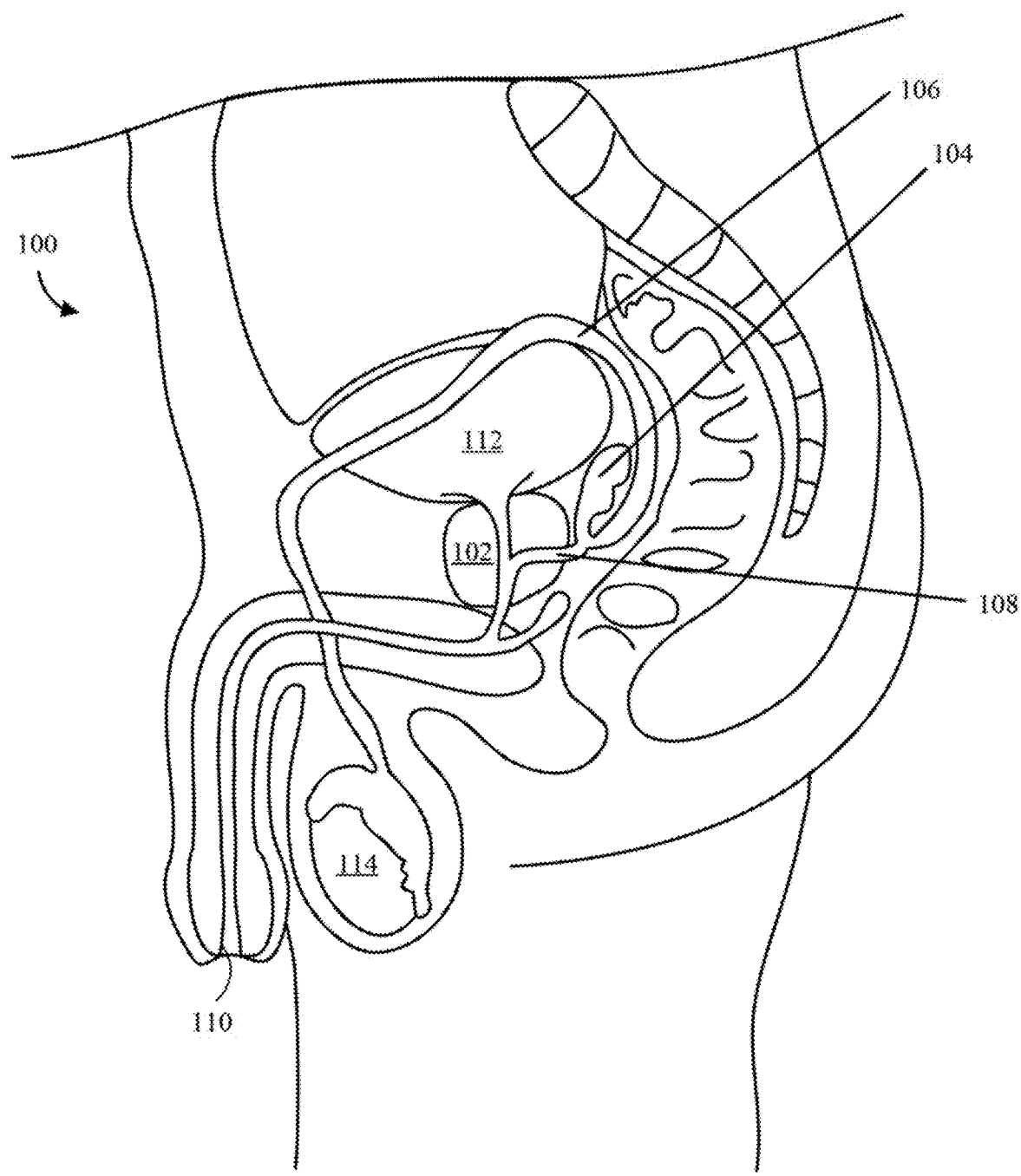
FIG. 1 is a side cross-sectional view of the male genitourinary system.
Figure 2:
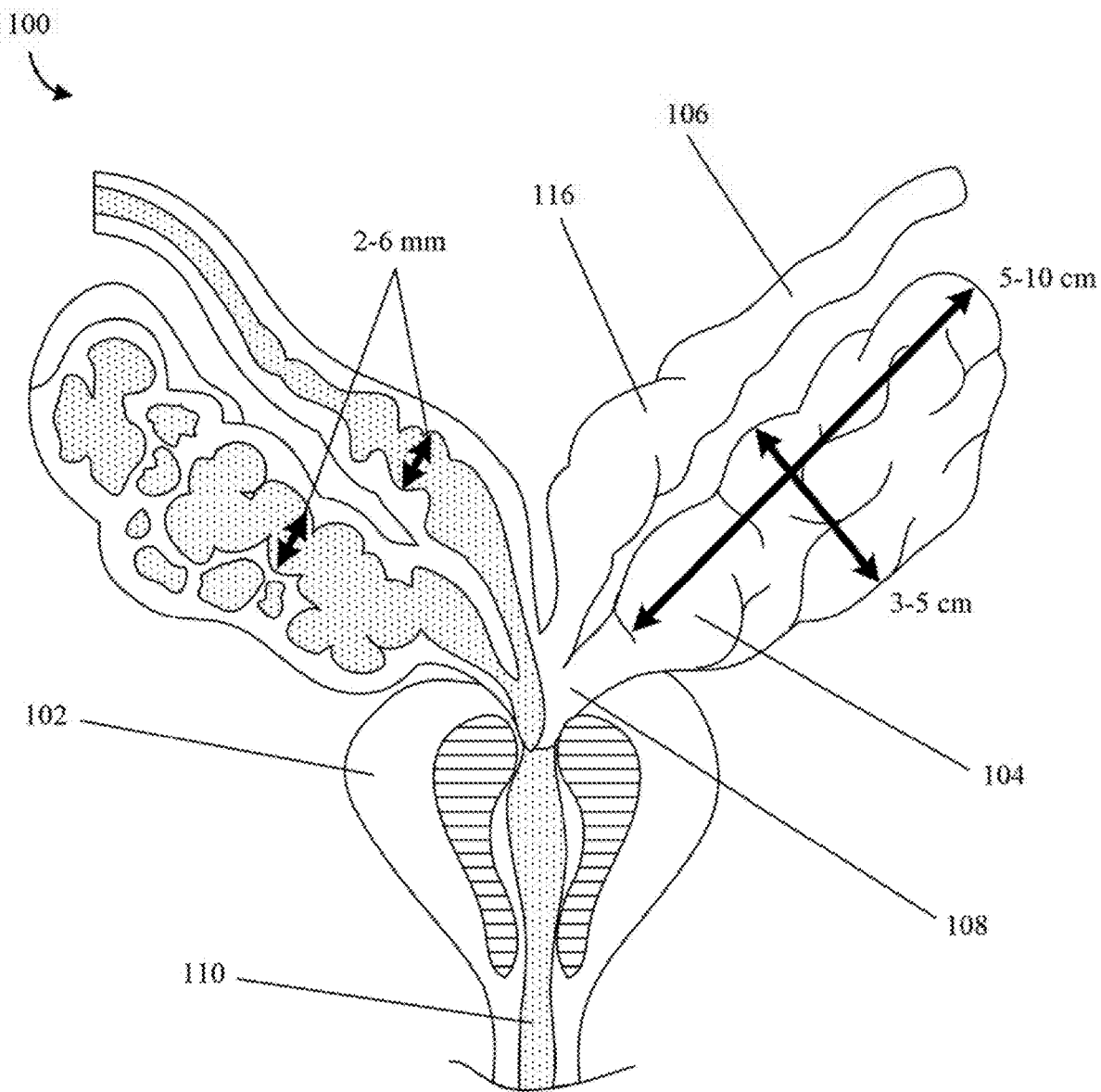
FIG. 2 is a front, partial cross-section view of a portion of the male genitourinary system.

FIG. 1 is a side cross-sectional view of the male genitourinary system 100, and FIG. 2 is a front, partial cross-section view of the male genitourinary system 100. As shown, the system 100 generally includes the prostate gland 102, seminal vesicles 104, vas deferens 106, the ejaculatory duct 108, the urethra 110, the bladder 112, and testes 114. The prostate gland 102 surrounds the urethra 110 just below the bladder 112. The seminal vesicles 104 are a pair of coiled, tubular glands that include inner ducts or lumens and outer pouches surrounding the lumens. The pouches are lined by columnar epithelium with goblet cells, as shown in FIG. 2. The gland is encased in a thin layer of smooth muscle and held in a coiled configuration by loose adventitia. The seminal vesicles 104 form lateral outpouchings of the ampulla 116 of the vas deferens 106. The vas deferens 106 are tortuous ducts that connect the epididymis of the testes 114 to the ejaculatory duct 108. The seminal vesicles 104 and the ampulla 116 of the vas deferens 106 are located posterior to the bladder 112 and are separated from the rectum by Denonvilliers' fascia, as shown in FIG. 1. In the adult human male, each seminal vesicle 104 is normally about 5-10 cm in length and about 3-5 cm in diameter, with an average volumetric capacity of about 13 mL, while inner ducts or lumens through the seminal vesicles 104, the vas deferens 106, and the ejaculatory duct 108 may be about 1-6 mm in diameter, as shown in FIG. 2. For example, inner ducts through the ampulla 116 may be about 2-6 mm in diameter, inner ducts through the vas deferens 106 may be about 3-5 mm in diameter, and inner ducts through the ejaculatory duct 108 may be about 2 mm in diameter or less.

In one aspect, an implantable medical device is provided that is dimensioned and has an elasticity suitable for deployment into and retention in a genitourinary tissue site in a patient. In one embodiment, the device includes a (i) resorbable, elastic device body having at least one elongated sidewall and at least one payload reservoir defined therein; and (ii) a payload stored in the payload reservoir. In one embodiment, the sidewall of the device body is selectively permeable to water and impermeable to the payload. In a particular embodiment, the implantable medical device is dimensioned and has an elasticity suitable for deployment into and retention in a prostate, a seminal vesicle, an ejaculatory duct, or a vas deferens in a patient. In one embodiment, the device is sized and shaped to fit into a 14 gauge needle. In another embodiment, the device is configured to be passed through a catheter, such as a urethral catheter, a cannula, or a cystoscope. For example, the device may be capable of being urged through a catheter or cannula by a stylet. In one example, the device body is configured for passage through an at least 16 Fr Foley catheter. In one case, the device may be in a folded configuration for passage through the catheter.

In another aspect, an osmotic pump device is provided that has a housing made of a bioresorbable elastomer and at least one aperture, and a drug contained in the housing. The bioresorable elastomer may be or include a poly(glycerol-sebacic acid) ("PGS"). In one embodiment, the osmotic pump device is dimensioned and has an elasticity suitable for deployment into and retention in a seminal vesicle, ejaculatory duct, vas deferens, or ampulla in a patient.

In one embodiment, the device body is in the form of an elongated hollow tube. In one example, the device body has an outer diameter between about 0.6 mm and about 3 mm, such as between about 1 mm and about 1.5 mm; and has a length between about 1 cm and about 7 cm, such as between about 1 cm and about 1.5 cm. In this or other examples, the sidewall of the device body may have a thickness between about 100 µm and about 600 µm, such as between about 400 µm and about 600 µm.

In one embodiment, the device body is in an elongated shape, such as a tube. It may have an exterior profile that is substantially cylindrical, with ends being both rounded, both flat, or a combination of these and other configurations. The device body also may have a more complex profile to facilitate its retention at the site of deployment. For example, the shape of the device body may include a portion tapered in an axial direction. For instance, the device may have a bullet, torpedo, or conventional suppository shape. The device body may also be ring shaped or annular shaped. The device should not add significant resistance to the passage of the seminal fluid and its constituents when implanted in the genitourinary site, such as the seminal vesicle, ejaculatory duct or ampulla.

The device body preferably is small and elastic. Such a configuration permits inserting the device body into an administration device, such as a catheter of a urethral cystoscope or a transrectal needle. The elasticity of the device also permits the device body to conform to the inner structures of the implantation site, such as the seminal vesicle, the ejaculatory duct or the vas deferens (e.g., ampulla). Thus, irritation to the tissues at the implantation site may be reduced.

In one embodiment, the device body is comprised of two or more elongated segments connected together. For example, the segments may be coupled in axial alignment by a flexible tether.

In various preferred embodiments, the resorbable, elastic device body is formed of or includes an elastomeric polymer, i.e., an elastomer. In one embodiment, the elastomeric polymer comprises a hydrophobic elastomeric polyester.

In a preferred embodiment, the polymer is a biocompatible condensation polymer of glycerol and a diacid, such as described in U.S. Patent Application Publication No. 2003/0118692 to Wang et al., which is incorporated herein by reference. In one preferred embodiment, the elastomeric polymer comprises a poly(glycerol-sebacic acid). It advantageously has the combination of physical, chemical, and mechanical properties for forming the device bodies described herein, including: 1) degradation via hydrolysis of ester bonds into alcohol and acid monomers; 2) crosslinking bonds identical to those in the polymer backbone; 3) non-toxic monomers, one with tri-functionality to provide cross-linking capability and one with hydroxyl groups to provide additional mechanical stability via hydrogen bonding. Glycerol, with its tri-functionality, hydroxyl groups, and biocompatibility, functions as the primary building block for the synthesis of lipids in vivo. Sebacic acid, as the acid monomer, has a desirable chain length (i.e. long enough not to cyclize during polymerization and short enough to mix well with glycerol), functions as the natural metabolic intermediate in ω-oxidation of fatty acid chains, and has been shown to be safe in vivo. Products containing both glycerol and sebacic acid have been approved by the FDA for use in medical applications.

In alternative embodiments, the bioresorable elastomeric polymer may comprise a poly(caprolactone) (PC) derivative, a poly(anhydride), an amino alcohol-based poly(ester amide) (PEA), or a poly(octane-diol citrate) (POC), although synthesis of the polymer may have to be adjusted to achieve the desired biodegradation characteristics and elastic properties.

In various embodiments, the device body provides controlled release of the payload in vivo by dispensation through one or more apertures in the device body, by diffusion through the sidewalls, by surface erosion of all or a portion of the device body, or a combination thereof.

In some embodiments, the device body includes one or more apertures that function as release orifices. The aperture may be at an end of the device body or in a side wall of the device body, or a combination thereof. Two or more discrete apertures may be provided in selected positions through the outer surface of the device body. The apertures may be formed by, for example, precision machining, mechanical punching, laser drilling, or by molding. The apertures may be microscale in size, which may be required for effective osmotic release of drug from the payload reservoir. The apertures may also be one or more open ends of an elongated housing in communication with a payload reservoir formed in the interior of the housing. The size of the device can influence or determine the release kinetics. In one embodiment, the diameter of the one or more apertures is between about 20 µm and about 300 µm. In one particular embodiment, the diameter of the one or more apertures is between about 80 µm and about 170 µm. In one further embodiment, the diameter of the one or more apertures is between about 100 µm and about 150 µm. In one optional embodiment, the apertures initially are sealed until a time after the device is implanted in the patient. For example, the device body may include a degradable membrane in register with at least one of the one or more apertures, wherein the membrane degrades in vivo at a faster rate than the device body and/or the membrane degrades in vivo enough to rupture before the device body can degrade enough to rupture.

In a preferred embodiment, release of the payload from the device in vivo is osmotically driven. For example, a majority of the drug, such as from about 60% to about 95% of the drug, is released in a controlled manner with an osmotic pressure driving force. Advantageously, this release mechanism is particularly suitable for drug delivery in the male genitourinary tract. The reason for this suitability is that the osmotic mechanism provides release at a constant rate in physiological systems involving significant pH gradients, such as the male genitourinary tract, because osmotic pressure is a constant driving force independent of changes in pH. In another embodiment, a majority of the drug may be released by an osmotic pressure mechanism in combination with another release mechanism, such as diffusion. For example, osmotic pressure may drive the drug release during an initial delivery period, while diffusion may augment or dominate the drug release thereafter. In one such embodiment, about 30% of the drug is released due to osmotic pressure during an initial delivery period, while the remainder of the drug is released due to osmotic pressure and diffusion thereafter. In another embodiment, release of the payload from the device in vivo occurs primarily or entirely by diffusion. In some embodiments, the predominate release mode may change over time following in vivo implantation, for example, as the drug reservoir is depleted of drug, as the device body disintegrates, or a combination thereof.

The payload reservoir or drug reservoir may be a hollow space within an interior of the device body, defined by an interior surface of the device body wall. For example, the reservoir may be a central bore in an elongated annulus shaped device. In some cases, the device may include two or more separate payload reservoirs. For example, the otherwise continuous bore within a single device body may be segregated into discrete compartments by one or more partitions perpendicular to the axis of the annulus. In another example, the device body may have multiple lumens. These may be arranged side-by-side, e.g., made by an extrusion process.

In a preferred embodiment, the payload in the device body comprises one or more drugs. The drug may be a chemical or a biologic. Alternatively, the payload may deliver a substance other than a drug, such as a diagnostic agent or a placebo. Two or more drugs may be stored together in a single reservoir. Alternatively, two or more drugs may be stored in two or more separate reservoirs in a single device.

In some preferred embodiments, the one or more drugs are useful for treating chronic prostatitis, seminal vesiculitis, post-prostatectomy complications, or cancer, such as a cancer of the prostate gland, the bladder, the rectum, or surrounding areas including the seminal vesicles. In one embodiment, the drug comprises an antibiotic agent, such as a fluoroquinolone. In a preferred embodiment, the fluoroquinolone comprises ciprofloxacin or levofloxacin. In some other embodiments, the drug comprises an immunosuppressant, an anti-inflammatory agent, a chemotherapeutic agent, a local anesthetic, an alpha-blocker, or a combination thereof. Other drugs also may be included in the device. The drug may be in a substantially pure form or formulated with one or more pharmaceutically acceptable excipients, which are known in the art.

The drug formulation may be in a concentrated or pure form, such as a solid, semi-solid, or gel, so as to contain in as small a volume as possible enough drug for release over the extended period required for a particular therapeutic indication. The solid form may be a compacted powder. The drug may be in a lyophilized form. In other embodiments, the drug may be in the form of a pure liquid, a suspension, emulsion, or solution.

In one embodiment, the drug is in the form of a hydrochloride or other pharmaceutically acceptable salt. For example, the hydrochloride salt form of the ciprofloxacin has a significantly higher water solubility than the plain form, which makes the salt form more suitable as an osmotic agent for an osmotic pump device. In one embodiment, the drug or other payload substance has a water solubility between about 30 and about 300 mg/mL at 37° C.

In one particular embodiment, an implantable drug delivery device is provided which is dimensioned and has an elasticity suitable for deployment via urethral catheter or transrectal injection into and retention in a seminal vesicle, ejaculatory duct, or vas deferens (e.g., ampulla) in a patient, wherein the device includes (i) an elongated, resorbable, elastic device body housing at least one drug reservoir and being composed of a hydrophobic elastomeric polyester which degrades in vivo by surface erosion, for example with a disintegration half life of between about 1 week and 6 weeks; and (ii) at least one drug formulation in the drug reservoir, wherein the device provides controlled release of the drug in the seminal vesicle, ejaculatory duct, or vas deferens. The device body may include at least one aperture and may have side walls that are water permeable and selectively permeable to the drug, such that the device provides osmotically controlled release of the drug dispensed from the at least one aperture. In a preferred embodiment, the hydrophobic elastomeric polyester includes or consists essentially of a poly(glycerol-sebacic acid).

Figure 3:
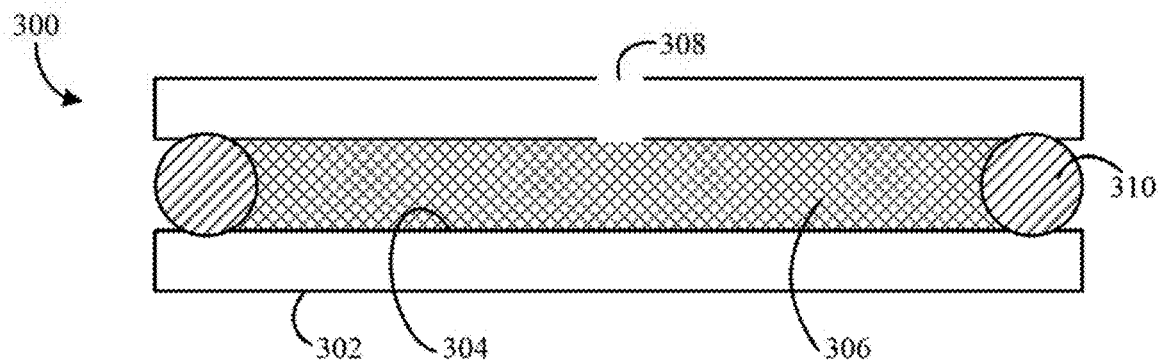
FIG. 3 is schematic cross-sectional view of an embodiment of a drug delivery device.

For example, FIG. 3 is a cross-sectional view of an example embodiment of a drug delivery device 300. As shown, the drug delivery device 300 includes a device body 302 or housing that defines a reservoir 304 or inner core. The device body 302 is configured to retain or hold a drug 306 or other payload in the core or reservoir 304 for release into an implantation site over an extended period of time. The drug 306 or payload may be released through one or more apertures 308 or release orifices in the sidewall of the device body. In addition, one or more plugs 310 or stops are provided to impede the drug 306 from escaping through ends of the device body 302.

The device body 302 and reservoir 304 may have any suitable shape or configuration. For example, the illustrated device body 302 and reservoir 304 are both substantially cylindrical in shape. Particularly, the device body 302 includes a generally tubular sidewall that defines generally cylindrical exterior and interior surfaces. The interior surface of the sidewall defines the boundary of the reservoir 304 or core, which is substantially hollow or empty for loading with the drug 306 or payload. The apertures 308 or release orifices, if any, may be formed through the sidewall, extending from the exterior surface to the interior surface. The apertures 308 may also be defined by open end portions of the device body 302. The device body 302 also may be closed along the open end portions by one or more plugs 310 or stops. The plugs or stops 310 may prevent any drug 306 within the core 304 from escaping through end portions. The plugs 310 or stops may have a range of configurations. For example, the plugs 310 or stops may be small objects, such as spheres, discs, or balls, that substantially span the cross-section of the core 304. Example materials that may be used to form the plugs 310 include bioresorbable polymers of the type described below, or other materials such as stainless steel. In preferred embodiments, the plugs 310 may be slightly larger in cross-section area than the cross-sectional area of the core 304. In such embodiments, the device body 302 may frictionally engage the plugs 310 to hold them in place. In some embodiments, plugs 310 or stops may also be positioned along the length of the core 304 to divide the core into multiple discrete reservoirs 304, which may be loaded with the same or different drugs 306. In such embodiments, multiple discrete apertures 308 may be located along the length of the device body 302 such that at least one aperture is associated with each of the reservoirs 304. It should be noted that the apertures 308 may also be formed through one or more of the plugs 310 in some embodiments. The illustrated embodiment is merely one example of a shape and configurations that may be employed, as a person of skill in the art could envision a variety of other configurations.

In one embodiment, the device body 302 has no associated retention features. In this case, the device body 302 is retained at the deployment site in vivo through frictional engagement with surrounding tissue of the site, such as the seminal vesicle, prostate, vas deferens or ejaculatory duct. For example, the device body 302 may be at least partially embedded within tissue of the deployment site in vivo. As another example, the device body 302 may be at least partially implanted within a lumen of the deployment site in vivo, and at least a portion of the outer surface of the device body 302 may contact or engage at least a portion of the inner surface of the lumen to create friction. In such cases, at least a portion of the device body 302 may have a cross-sectional area or shape that exceeds or differs from the normal cross-sectional area or shape of the lumen, facilitating the creation of friction. The tissue in the implantation site may expand to permit insertion of the device via catheter or injection, and once implanted the tissue may relax or return to hold the device 302 in place within the lumen.

In other embodiments, the device body 302 may be configured for retention within the deployment site in vivo. For example, the device body 302 may have one or more retention features. In embodiments, the device body 302 may optionally have an elastic retention frame, which retains the device in a genitourinary site. The retention frame may have a number of shapes for retention, including hoop, coil, spring, 2-D spiral, or 3-D spiral shapes. In other embodiments, the device body 302 itself may have one or more of these shapes. The device body 302 may also be associated with separate retentive features. For example, the device body 302 may be a linear shape with flexible and extendible projections, anchor-like structures such as wings or legs, or structures that change shape or configuration to assume a lower-profile shape for insertion and a higher-profile shape upon implantation. These retentive features may be included but typically would be omitted for devices intended for deployment in other lumenal tissue sites, such as the seminal vesicle, ejaculatory duct, or the ampulla, or in non-lumenal tissue sites.

The material used to form the device body 302 may be selected so that the device body 302 is one or more of the following: elastic, biocompatible, resorbable, suitably mechanically and structurally sound, and at least partially permeable. A device body 302 that is elastic may be suited for inserting through a bore of a catheter or a needle into a patient and for retention in the patient without significant irritation or discomfort. Such a device body 302 may stretch and deform during and after implantation, without experiencing unsuitable yielding or failure that impacts drug delivery. The elasticity may be achieved by formation of the device body from an elastomeric polymer (i.e., an elastomer). A device body 302 that is biocompatible may be tolerated by the patient throughout the duration of implantation. A device body 302 of suitable mechanical strength and structural integrity may facilitate reliable and consistent drug release throughout the duration of therapy. A device body 302 that is resorbable may naturally degrade or erode in time, eliminating the need for removal or extraction. In some embodiments, the device body 302 may begin degrading or eroding once implanted in the body, yet the configuration of the device body 302 may be such that the device body 302 maintains suitable mechanical strength and integrity over the duration of therapy. Such a configuration may be obtained by selecting the materials and dimensions of the device body 302 in view of the intended implantation site and duration of therapy. For the purpose of this disclosure, the term "duration of therapy" indicates the period of time over which a drug 306 is emitted from the device 300, while the term "duration of implantation" indicates the period of time over which the device 300 is implanted in the body before completely eroding. The duration of implantation may exceed the duration of therapy, so that the drug is substantially completely released from the device 300 before the device 300 experiences an unsuitable degree of erosion.

A device body 302 that is at least partially permeable may be suited for generating an osmotic pressure in the core or reservoir 304, permitting the device 300 to operate as an osmotic pump. In a preferred embodiment, the device body 302 is permeable to water or other fluid without dissolving, degrading, or swelling in response to the presence of water or other fluid, which may facilitate implanting the device 300 for release of the drug 306 over an extended time period, without the device failing, at least without failing prior to completion of the intended, controlled drug delivery functionality.

In one embodiment in which the device body 302 is at least partially permeable, the device 300 operates as an osmotic pump. Particularly, the device body 302 may be selectively permeable to water or other bodily fluids so that such fluids may permeate through the device body 302 to the reservoir 304. Once in the reservoir 304, the fluid may solubilize a drug 306 or payload housed therein. The fluid may create an osmotic pressure in the core or reservoir 304 to drive the drug 306 or payload from the device body 302, such as through any apertures 308. In a preferred embodiment, the device body 302 is suitably permeable to water while being substantially or negligibly impermeable to the drug 306 in the reservoir 304. In such embodiments, the device 300 may be suited to facilitate a controlled, substantially constant release of the drug 306 throughout at least a substantial portion of the duration of therapy. Such a device body 302 may be semi-permeable or "permselective."

In preferred embodiments in which the device body 302 operates as an osmotic pump, the drug 306 is released through the apertures 308. The apertures 308 may also permit release of the drug 306 in other embodiments, such as those in which the device 300 operates via diffusion. The size, shape, and location of the apertures 308 may at least in part determine the release profile for the drug 306. Thus, the size, shape, and location of the apertures 308 may be selected to achieve a desired release profile in some embodiments, along with the material used to form the device body 302, the shape and dimensions of the device body 302, the characteristics of the drug 306, the implantation site, and the intended duration of therapy. In some embodiments, the device 300 further includes one or more degradable membranes. The degradable membranes may initially be in registration with at least one of the one or more apertures 308. Once implanted, the degradable membranes may degrade more quickly than the device body 302 to permit release of the drug 306.

One type of material that can be used to form the device body 302 is an elastomeric polymer, such as a poly(caprolactone), a polyanhydride, an amino alcohol-based poly(ester amide), or a poly(octane-diol citrate). Other suitable materials for the device body 302 include hydrophobic polymers that degrade via surface erosion, such as polyorthoesters, or biocompatible and resorbable materials, such as polyactide, polyglycolide and their copolymers (PLA, PGA and PLGA). Still other materials, or combinations of these and other materials, may be used for the device body 302.

One particularly suitable material is a hydrophobic elastomeric polyester that degrades by surface erosion, such as poly(glycerol-sebacic acid) ("PGS"). PGS is generally elastic, biocompatible, resorbable, suitably mechanically and structurally sound, selectively permeable, and hydrophobic. Particularly, PGS may degrade in vivo by surface erosion into biocompatible monomers, yet PGS may maintain mechanical strength and integrity even after the experiencing significant erosion. For example, PGS implanted in vivo in rat has been shown to have a half-life of about three weeks while retaining about 75% of its original mechanical strength. When formed from PGS, the device body 302 may be configured such that the duration of therapy ends before the device body has eroded to the point of substantial mechanical impairment or failure. Additionally, a device body 302 formed from PGS may not experience significant swelling or induce the formation of significant fibrous capsules in the body once implanted.

In embodiments in which the device body 302 erodes or degrades in vivo, it generally is not be necessary to configure the device body 302 for retrieval. For example, the device body 302 may lack retrieval features, such as rings, springs, coils, or pigtails, that facilitate grasping the device body 302. Also, retrieval may not be a significant factor, or may be ignored completely, when selecting the geometry of the device body 302. For example, a device body 302 that is relatively linear and substantially cylindrical may lack a retrieval feature and yet may be suited for implantation in a site such as a seminal vesicle, a vas deferens, an ejaculatory duct, or a prostate.

The device 300 may be sized, shaped and configured for implantation into a genitourinary site of a human male. For the purposes of this, the term "genitourinary site" is intended to connote any site within the genitourinary system, including any portion of the prostate gland, the seminal vesicles, the vas deferens, the ejaculatory duct, the urethra, the bladder, and the testes. In preferred embodiments, the device 300 is sized, shaped and configured for implantation within a lumen or duct of the genitourinary system, such as in a lumen or duct of one of the seminal vesicles, vas deferens, ejaculatory ducts, or the urethra. The device 300 may also be sized, shaped and configured for embedding directly within a non-lumenal tissue site of the genitourinary system, such as directly in the prostate gland or the tissues of the seminal vesicles. Due to its elastic nature, the device body 302 in such an embodiment may deform to fit the shape of the implantation site and may give to permit the passage of bodily fluids through the implantation site, such as seminal fluid or its constituents components. The elastic nature of the device 300 also may permit folding the device body 302 in some embodiments for implantation through a needle or cannula. Once implanted, the device 300 may naturally return following implantation into an unfolded position.

In some embodiments, the device 300 is sized, shaped, and configured for implanting into a patient through a bore of a hollow needle or cannula. For example, in embodiments in which the device is implanted in a genitourinary site, the device 300 may be implanted via urethral catheterization as described in further detail below with reference to FIG. 6, or via transrectal injection as described in further detail below with reference to FIG. 7. Typical urethral catheters for adult male patients are in the range of about 16 French to about 18 French, which corresponds to an outer diameter of about 5.3 mm to about 6.0 mm, while typical transrectal needles for adult male patients are in the range of about 14 gauge to about 18 gauge, which corresponds to an inner diameter of about 1.07 mm to about 1.6 mm. Thus, the device may have an outer dimension that is less than about 4 mm for insertion via a urethral catheter or less than about 1.5 mm for insertion via a transrectal needle.

The length of the device 300 may be selected based in part on the size and shape of the implantation site and the amount of drug 306 to be delivered. For example, a longer device 300 may have a larger reservoir 304, which may permit implanting a larger payload and releasing larger doses and/or the appropriate dosage of drug over longer sustained period.

One example device 300 may have an outer diameter between about 0.6 mm and about 3 mm, such as between about 0.6 mm and about 1.6 mm, and a length between about 1 cm and about 7 cm, such as between about 1 cm and about 1.5 cm. Such a device 300 may be suitable for insertion through a catheter or needle, such as a urethral catheter or a transrectal needle. Such a device may also be suited for implantation into a genitourinary site of an adult male patient, such as a lumen or duct of through one of the seminal vesicles, vas deferens, or ejaculatory ducts. In these and in other embodiments, the sidewalls of the device body 302 may have a thickness between about 100 μm and about 600 μm, such as between at least about 200 μm and about 300 μm, and the apertures 308 may have diameters of between about 20 μm and about 300 μm, such as between about 80 μm and 170 μm, or more particularly between about 100 μm and about 150 μm. Such dimensioning of the sidewalls and apertures may facilitate zero-order release of the drug 306 from the core 304 via an osmotic pressure driving force, as further described below.

The device 300 may be configured to release a drug 306 through the sidewall, from the sidewall, through the orifice 308, or a combination thereof. The device 300 may be configured to release the drug 306 via osmotic pressure, diffusion, surface erosion, or a combination thereof.

In embodiments in which the device 300 is configured to release the drug in vivo via diffusion, the diffusion may occur through one or more apertures 308, through the sidewall of the device body 302, or a combination thereof. Diffusion of the drug 306 may be driven by a concentration difference between the drug 306 in the reservoir 304 and the surrounding environment, such as the implantation site.

In embodiments in which the device 300 is configured to release the drug in vivo via surface erosion, the device body 302 may include one or more matrix materials. In one example, the one or more matrix materials may comprise one or more synthetic polymers. In another example, the one or more matrix materials may comprise biodegradable, bioerodible, or water-soluble matrix materials. The drug 306 may be distributed in the matrix material and the matrix material may degrade or dissolve in vivo to controllably release the drug. In such embodiments, the device 300 may or may not have a core or reservoir 304. In other such embodiments, the device 300 may include a core or reservoir 304, in which case a bolus dose of the drug may be released after the device body 302 degrades.

Figure 4:
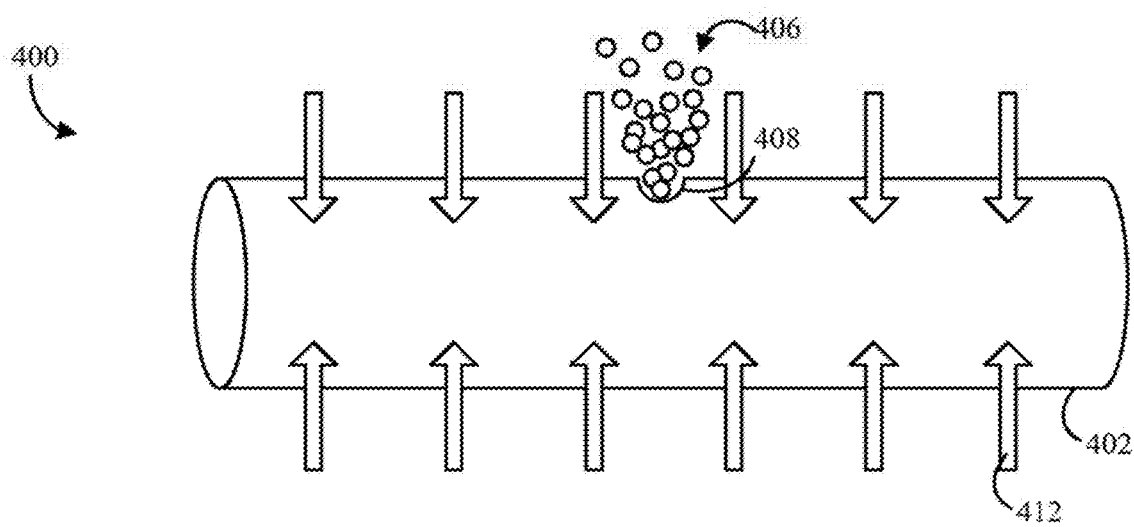
FIG. 4 is schematic cross-sectional view of another embodiment of a drug delivery device that functions as an osmotic pump.

In embodiments in which the device 300 is configured to release the drug 306 in vivo via osmotic pressure, the drug 306 may be released through the one or more apertures 308. An example is shown in FIG. 4. Once the device 400 is implanted in vivo, water or other bodily fluid 412 may permeate through the device body 402, such as through the sidewall. The water or fluid 412 may dissolve the drug 406 in the core, forming a solution of the drug 406. The hydrostatic pressure within the core may rise, which may expel the solution through the orifice 408.

Returning to FIG. 3, in embodiments, the device 300 may be configured for relatively zero-order release via osmotic pressure. For example, the device 300 may be configured to employ a substantially zero-order release rate for at least a portion of the duration of therapy. In one preferred embodiment, a majority of the drug load is released at a zero order rate. The term "zero-order release rate" indicates the drug 306 is released at a relatively constant rate. To achieve a zero-order release rate, the size and number of the apertures 308 and the thickness of the sidewall of the device body 302 may be chosen, along with other parameters of the device design. For example, each aperture 308 may be sized so that the aperture 308 is small enough to reduce or eliminate bulk diffusion through the aperture 308, and yet is large enough to relieve hydrostatic pressure within the core 304, which otherwise may cause the device 300 to experience hydrostatic deformation. In one such embodiment, the diameter of the one or more of the apertures 308 may be between about 20 and about 300 μm, and the thickness of the sidewalls of the device body 302 may be between about 100 μm and about 600 μm, so that the sidewalls are thick enough to withstand the internal hydrostatic pressure in the core 304.

Such a device 300 may be suited for operating as an osmotic pump to release one or more drugs into a genitourinary site of a patient. An osmotic delivery mechanism may permit zero-order release rates in physiological systems involving pH gradients, such as the gastro-intestinal tract or the genitourinary system, as changes in pH may not impact osmotic pressure. Thus, a relatively constant driving force may expel the drug even in the presence of a pH gradient.

The release rate may also be at least partially dependent on the solubility of the drug 306, formulation excipients, and the density (porosity) of the drug in the core 304. For example, the release may initially occur at a relatively zero-order rate, during which time the device 304 operates substantially via osmotic pressure, and subsequently the release may occur via, for example, a combination of osmotic pressure and diffusion. Drugs with lower solubility may have a higher percentage released at a zero-order release rate, but may release more slowly due to a lower osmotic pressure. Drugs having a higher solubility may release at faster rates, but a smaller percentage of the drug payload may be released at a zero-order release rate. In certain embodiments, the solubility of the drug 306 in water is between about 30 mg/mL and about 300 mg/mL at 37° C. For example, ciprofloxacin-HCl (CIP-HCl) has a solubility of about 0.03 g/mL, and in one embodiment exhibits zero-order release, driven by osmotic pressure, for about 97% of the drug. In another example, lidocaine-HCl (LIDO-HCl) has a solubility of about 0.68 g/mL and in one embodiment exhibits zero-order release, driven by osmotic pressure, for about 32% of the drug. Because CIP-HCl has a lower solubility, however, the zero-order release rate for CIP-HCl may be lower than the zero-order release rate for LIDO-HCL.

Figure 15:
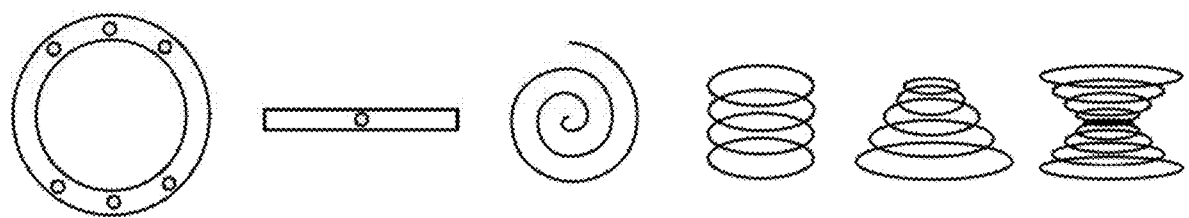
FIG. 15 shows examples of device embodiments for use in the bladder.

In another embodiment, the device is adapted for deployment and retention within the bladder. In this case, the device body may need to be configured in shape, and/or attached to an elastic retention frame, which retains the device in the bladder to prevent expulsion of the device during urination. In one case, such a device may be useful in the treatment of interstitial cystitis, overactive bladder syndrome, or bladder cancer. For retention, the device body may have a number of shapes including hoops, coils, springs, 2-D or 3-D spirals, or linear shape with flexible and extendible projections. Example embodiments are shown in FIG. 15. Specifically, the illustrated embodiments include a single loop shape with multiple orifices, linear shape with a single orifice, a spiral, and various 2-D and 3-D spirals, coils, and springs. In one embodiment, the device is configured to be elastically deformed from its initial shape into an elongated shape for passage through a catheter inserted into the urethra of a patient, and following said passage through the catheter to return toward its initial shape to facilitate retention of the device in the bladder of the patient.

In another aspect, methods are provided for delivering a payload to a genitourinary tissue site in a patient by deploying one of the implantable medical devices described herein to a patient in need thereof. The term "patient" may include humans, such as an adult male human, or other mammals. The implantable medical device may be implanted within a natural lumen within the genitourinary system, or alternatively the device may be implanted directly into a genitourinary tissue which is not at a lumenal site, e.g., the prostate gland.

Figure 5:
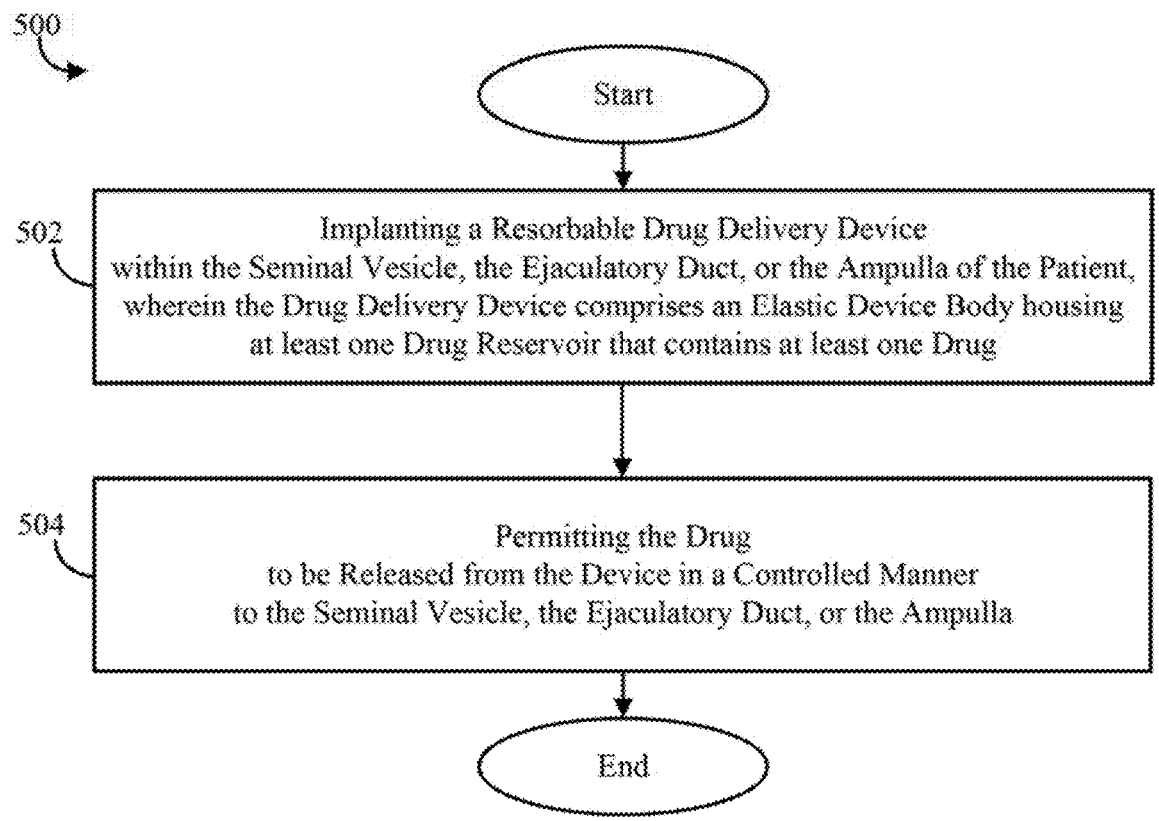
FIG. 5 is a block diagram illustrating an embodiment of a method of delivering a drug to a genitourinary site.

In a certain embodiment, a method 500 is provided for local delivery of a drug to a genitourinary site of a patient in need of treatment, such as to the seminal vesicle, the ejaculatory duct, or the vas deferens (e.g., ampulla) of the patient. FIG. 5 is a block diagram of the method 500. The method 500 includes, in block 502, implanting a resorbable drug delivery device within the seminal vesicle, the ejaculatory duct, or the vas deferens (e.g., ampulla) of the patient, wherein the drug delivery device comprises an elastic device body housing at least one drug reservoir which contains at least one drug; and in block 504, permitting the drug to be released from the device in a controlled manner to the seminal vesicle, the ejaculatory duct, or the ampulla.

In one embodiment, the step of implanting the resorbable drug delivery device in block 502 includes placement of a catheter in the urethra followed by cystoscopic deployment of the drug delivery device through the catheter. In an alternative embodiment, the step of implanting the resorbable drug delivery device in block 502 comprises transrectal injection. In either of these cases, the step of implanting the drug delivery device in block 502 may further include imaging and positioning of the drug delivery device, for example, by transrectal ultrasonography ("TRUS"), which is known in the art.

Figure 6A:
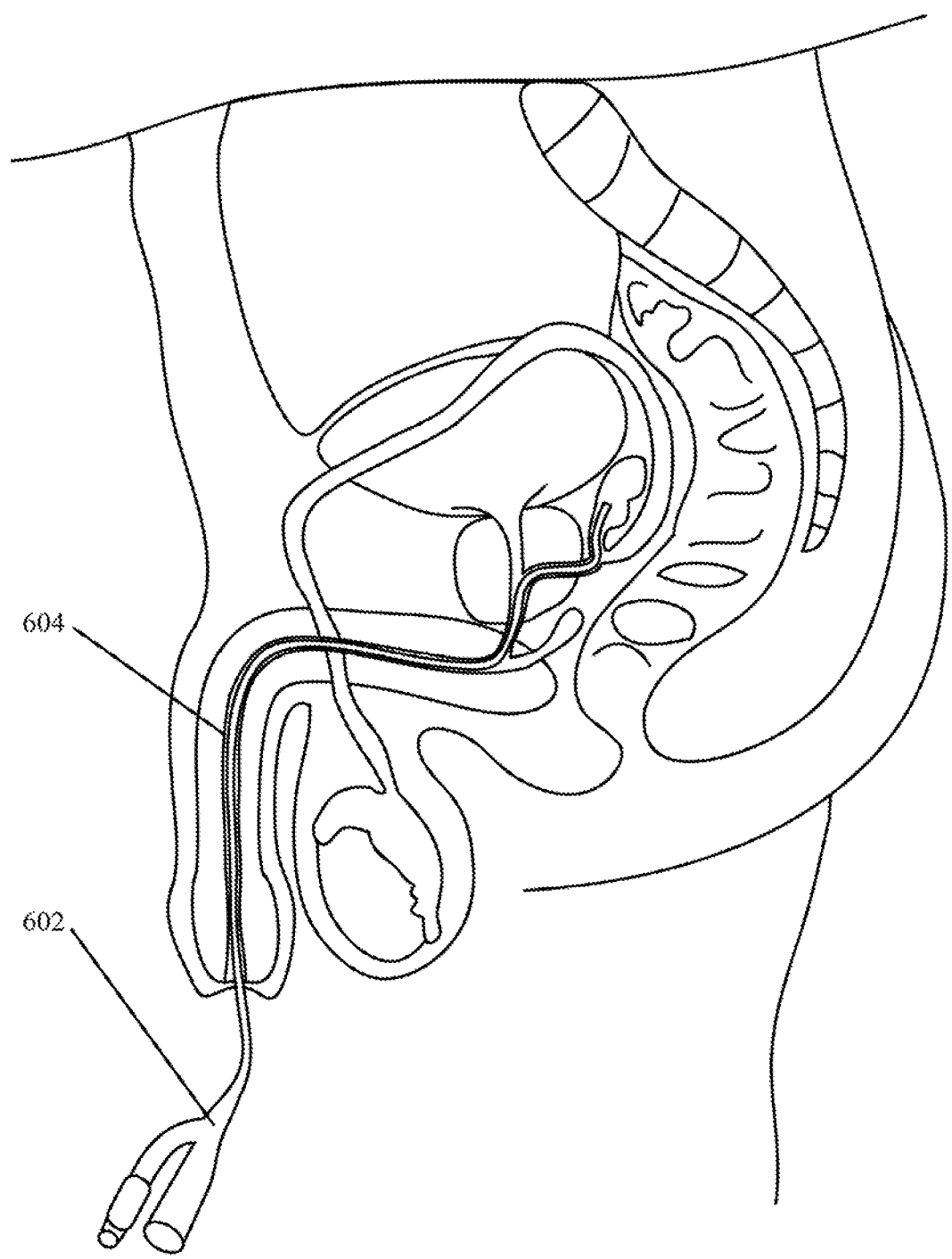
FIGS. 6A-6C are a series of side cross-sectional views of the male genitourinary system, illustrating a method of implanting a drug delivery device via urethral catheterization.
Figure 6B:
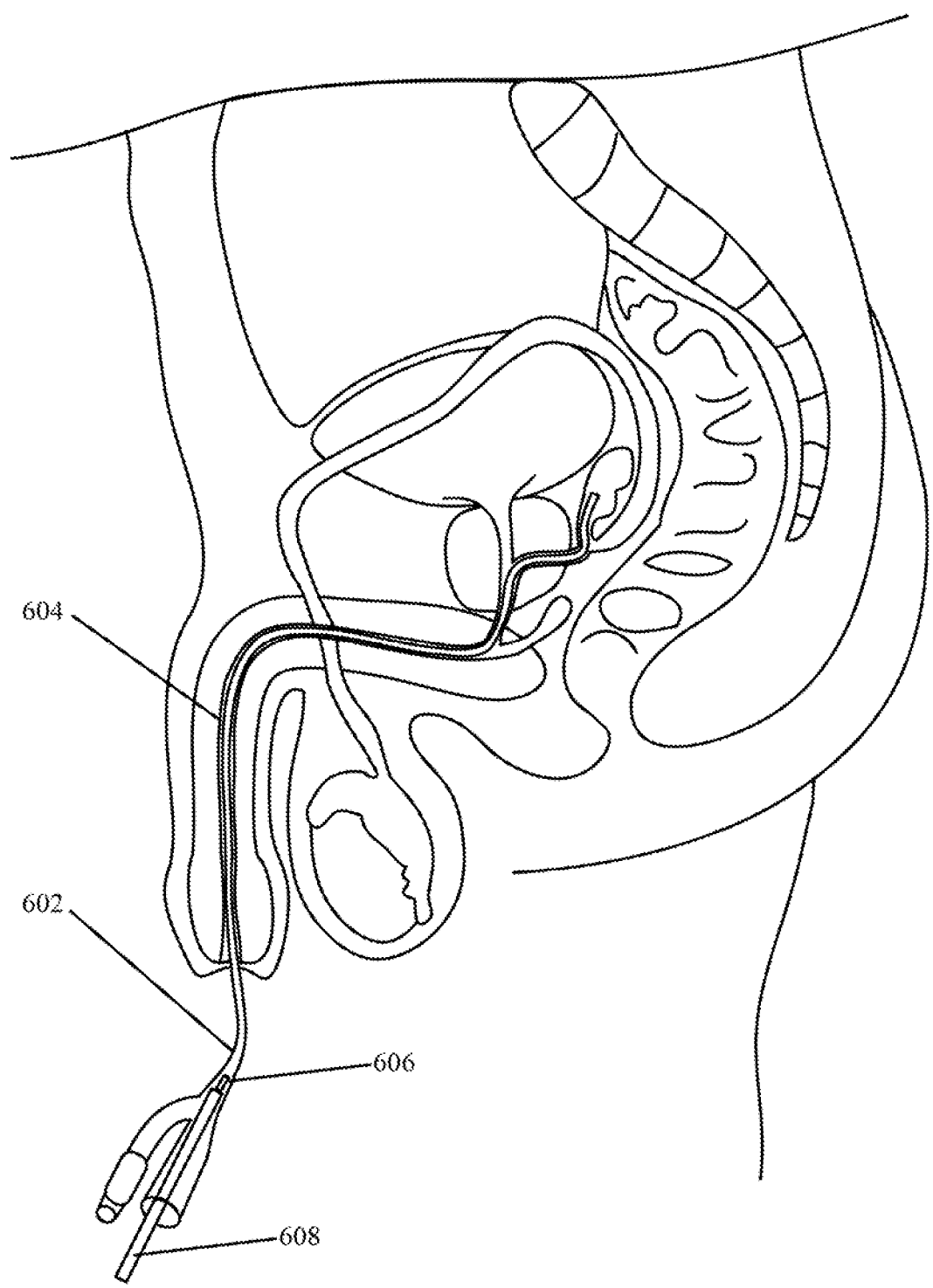
Figure 6C:
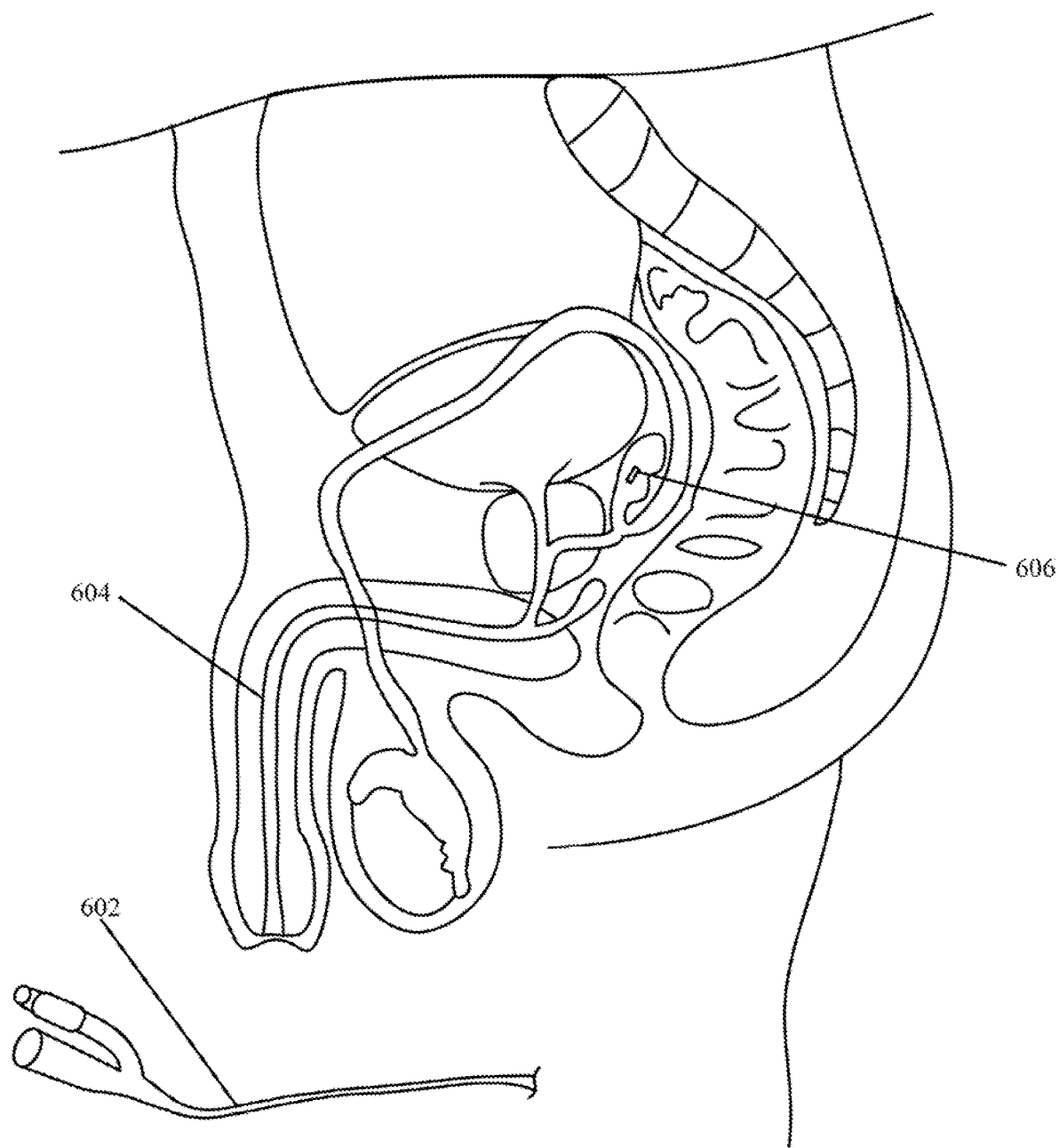

FIGS. 6A-6C are a series of side cross-sectional views of the male genitourinary system, illustrating an embodiment of the step of implanting a drug delivery device via urethral catheterization. As shown in FIG. 6A, a catheter 602 is placed in the urethra 604. The catheter 602 extends to the implantation site, which may be a site within the genitourinary system such as the prostate, the seminal vesicles, the ejaculatory duct, or the vas deferens. Although catheterization through the urethra is typically employed to access the bladder, it is noted that other portions of the anatomy may also be accessed along this route, as openings through the ejaculatory ducts into the seminal vesicles and the ampullae are accessible via the urethra. In certain embodiments, the catheter 602 is a 16-18 French unit Foley catheter. As shown in FIG. 6B, the drug delivery device 606 is inserted through the catheter 602 and is urged toward the implantation site using a stylet 608. In certain embodiments, insertion of the device may be guided using a cystoscope, TRUS, or a combination thereof. As shown in FIG. 6C, the catheter 602 is removed, leaving the device 606 implanted for controlled release of the drug in vivo to the implantation site and surrounding areas. Such an implantation step may be minimally invasive and may be performed in an outpatient setting, such as using a local anesthetic.

Figure 7A:
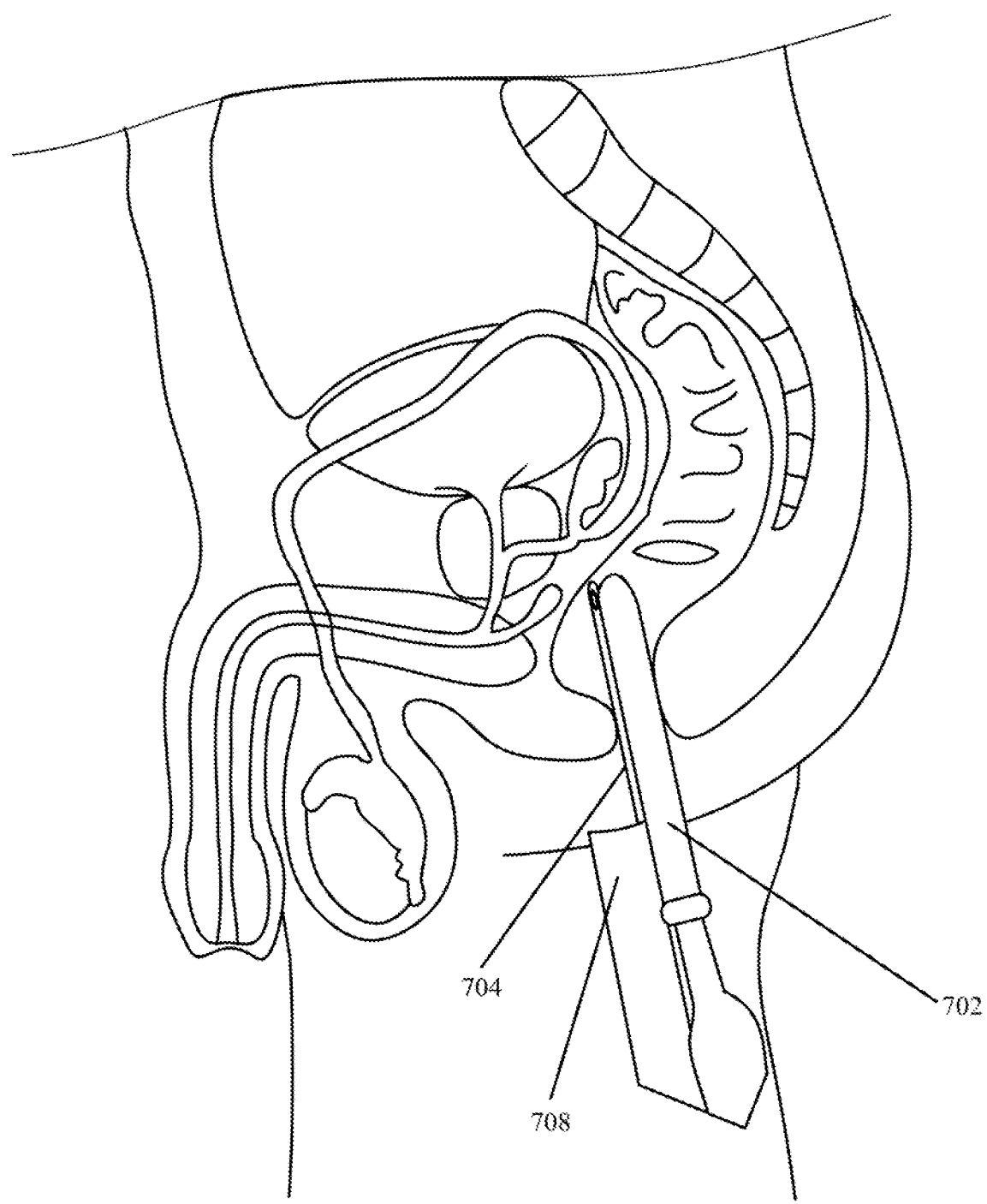
FIGS. 7A-7C are a series of side cross-sectional views of the male genitourinary system, illustrating a method of implanting a drug delivery device via transrectal injection.
Figure 7B:
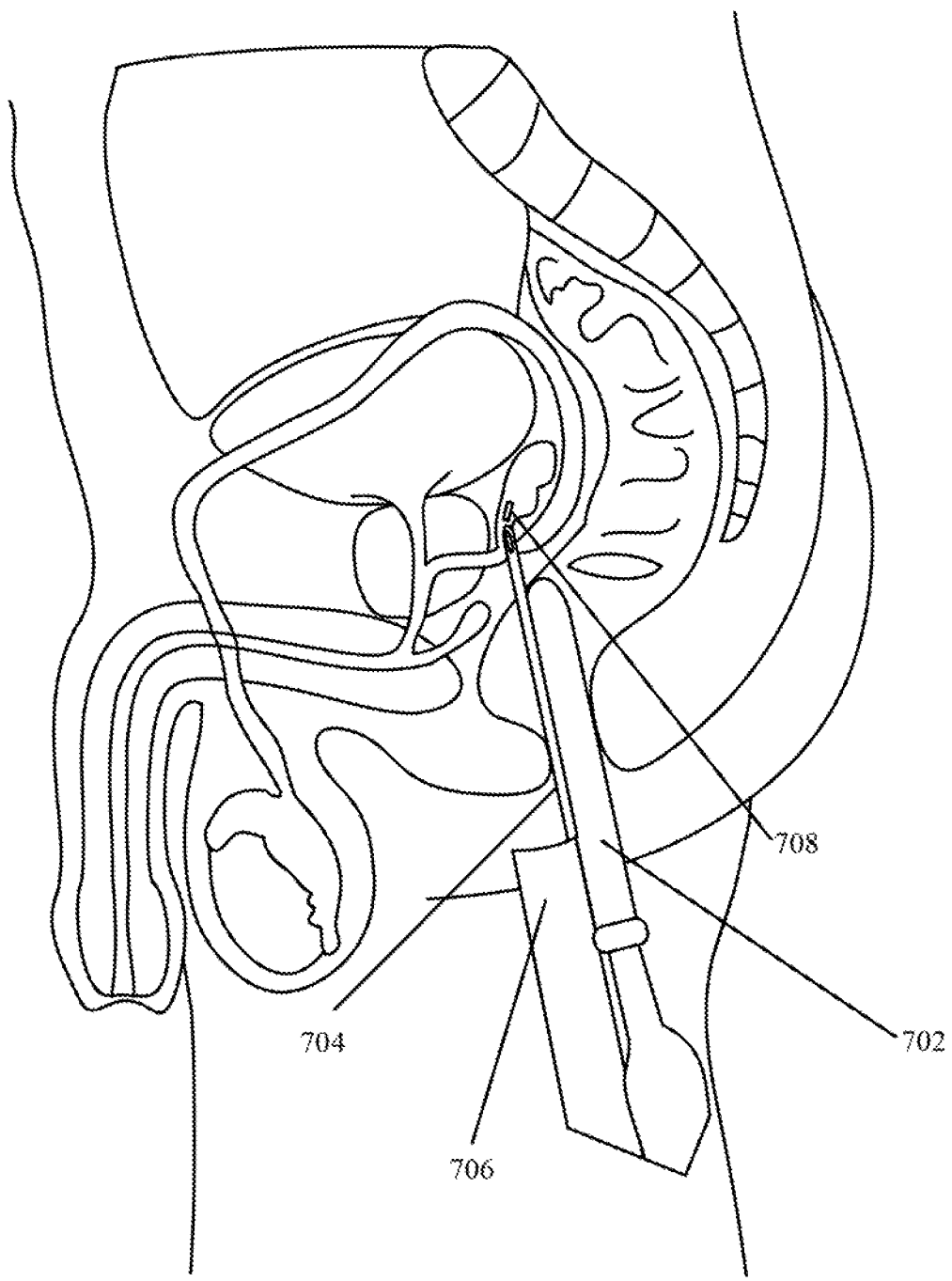
Figure 7C:
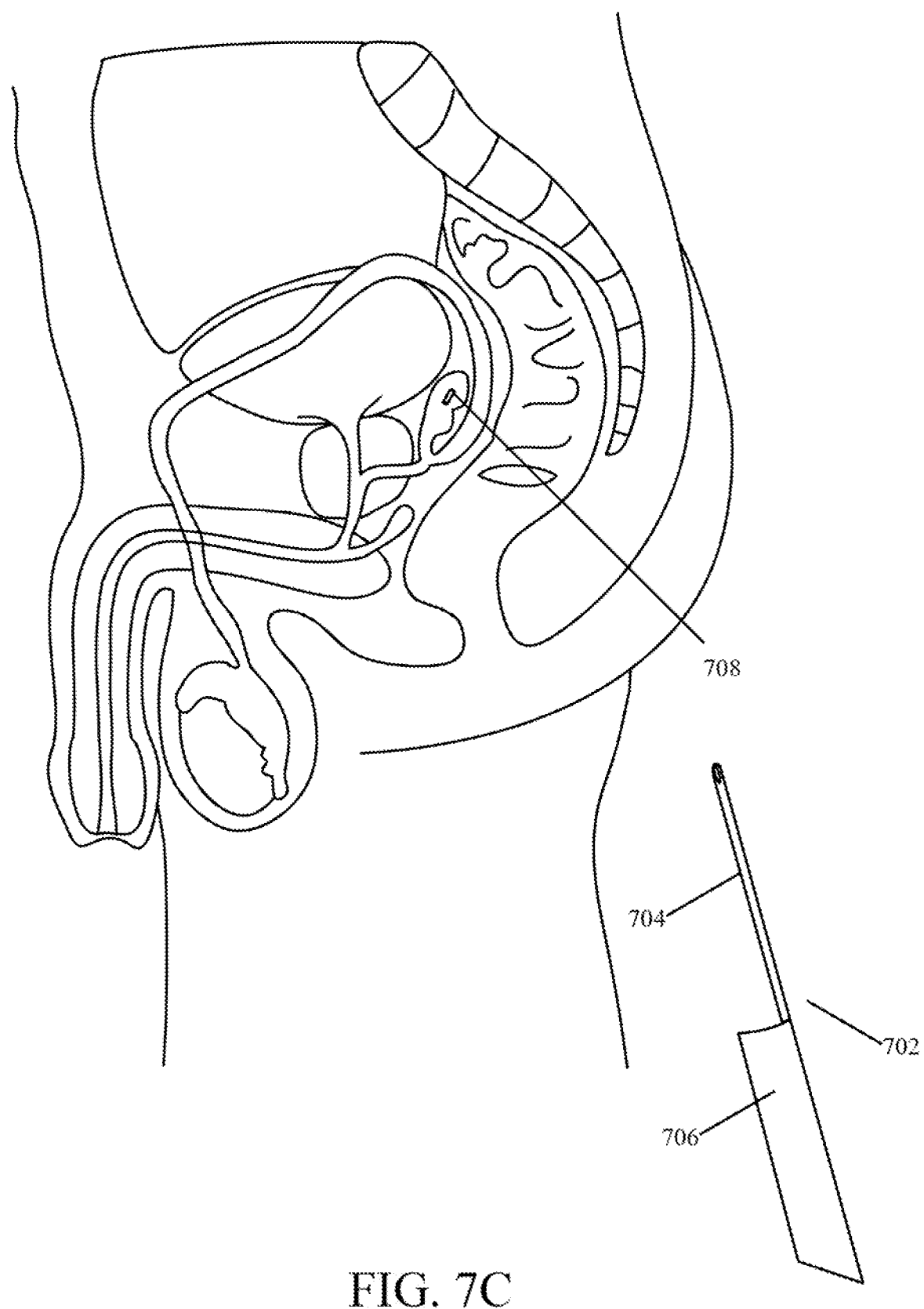

FIGS. 7A-7C are a series of side cross-sectional views of the male genitourinary system, illustrating an embodiment of the step of implanting a drug delivery device via transrectal injection. As shown in FIG. 7A, a rectal ultrasound probe 702 is positioned in the rectum. The probe 702 is positioned so that a transrectal needle 704 associated with a guide 706 of the rectal ultrasound probe 702 can access the implantation site through the anterior wall of the rectum. The implantation site may be any site within the genitourinary system, such as the prostate, the seminal vesicles, the ejaculatory duct, or the vas deferens. Although transrectal needles are typically employed to access the prostate through the anterior rectum wall, it is noted that other portions of the genitourinary system also may be accessed via this method, as the seminal vesicles, ampullae, and ejaculatory ducts lie adjacent to the rectum near the prostate. The transrectal needle may be in the range of about 18-gauge to about 14-gauge, depending on the embodiment. As shown in FIG. 7B, the drug delivery device 708 may be injected into the implantation site using the transrectal needle 704. In one embodiment, injection of the device 708 is guided using TRUS. As shown in FIG. 7C, the rectal ultrasound probe 702 and associated components are removed, leaving the device 708 implanted for controlled release of the drug in vivo to the implantation site and surrounding areas. Such an implantation step may be minimally invasive and may be performed in an outpatient setting, such as using a local anesthetic.

With reference back to FIG. 5, the release of the drug in block 504 may occur over a time period of about 2 days to about 4 weeks. For example, the drug may be released over a period of about 2 weeks to about 3 weeks in some embodiments.

In a preferred method, following release of substantially all of the drug in block 504, the device body degrades by surface erosion into biocompatible monomers. For example, the device may begin degrading upon implantation and may degrade while the drug is released. After the drug is released, the device may continue degrading to the point of loss of mechanical integrity. For example, the device may degrade over a time period of about 2 to about 8 weeks. In embodiments in which the drug is released over a time period of about 2 to about 3 weeks, the device may degrade over a time period of about 4 to about 8 weeks. Thus, the method 500 may further include permitting the device to degrade in vivo, which may avoid the need for removing or retrieving the device after the drug has been released. The method may be useful for example with a patient who presents with chronic prostatitis, vesiculitis, post-prostatectomy complications, or a cancer involving the prostate gland, bladder, or rectum.

Figure 8:
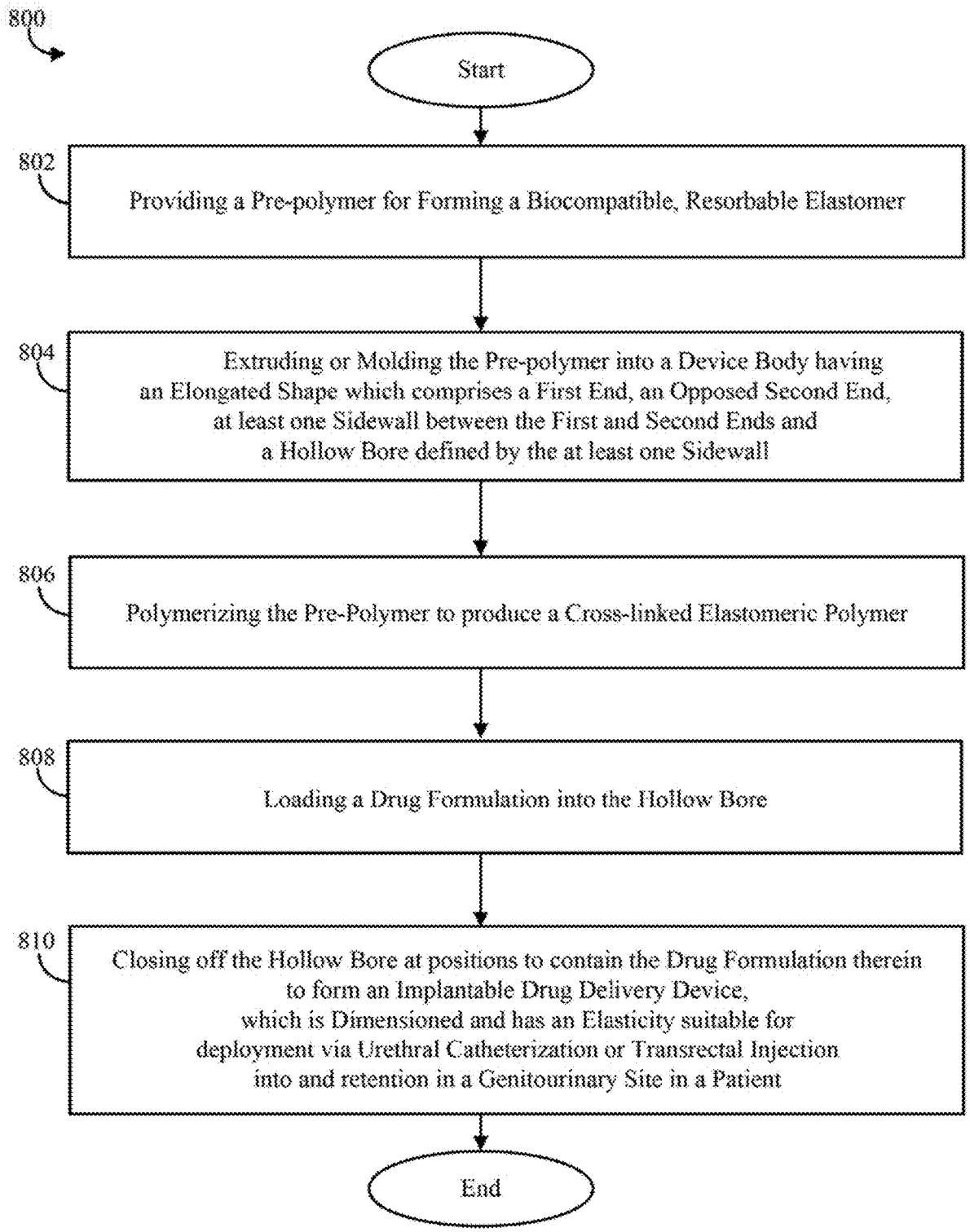
FIG. 8 is a block diagram illustrating an embodiment of a method of making a drug delivery device.

In another aspect, a method 800 is provided for making an implantable drug delivery device. FIG. 8 is a block diagram illustrating an embodiment of the method 800. In one embodiment, the method 900 includes the steps of (i) providing a pre-polymer for forming a biocompatible, resorbable elastomer (block 802); (ii) extruding or molding the pre-polymer into a device body having an elongated shape which comprises a first end, an opposed second end, at least one sidewall between the first and second ends and a hollow bore defined by the at least one sidewall (block 804); (iii) polymerizing the pre-polymer to produce a cross-linked elastomeric polymer (block 806); (iv) loading a drug formulation in the hollow bore (block 808); and (v) closing off the hollow bore at positions to contain the drug formulation therein (block 810). The resulting implantable drug delivery device is dimensioned and has an elasticity suitable for deployment via urethral catheterization or transrectal injection into and retention in a genitourinary site in a patient. The method may further include forming one or more apertures in the sidewalls of the device body. In various embodiments, the apertures may be formed by laser microablation, by drilling, by molding, or by mechanical punching. In one embodiment, the step of closing off the hollow bore comprises inserting at least one plug element into the first end, the opposed second end, or both ends. The plug element may be made of the same material as the device body, or it may be made of another material, such as a resorbable polymer.

In one process, the device body may be formed by casting and cross-linking of a pre-polymer under controlled conditions of vacuum and/or heat. In order to form a payload reservoir in the device body, a wire may be positioned in the mold during the casting process. After the device body has cured, the device body may be removed from the mold and the wire may be removed from the device body. Thereby, the hollow payload reservoir is formed. In some cases, multiple device bodies may be molded simultaneously. A module may be cast using multiple wires to form multiple hollow cores, and after the module is released from the mold, the module may be cut into multiple device bodies. Thereafter, the orifice may be formed by, for example, laser microablation. In some cases, multiple orifices may be formed.

Alternatively, a high volume process can be used to make the device. For example, the device housing may be made extrusion, for example, onto a cylindrical wire template or using an annular-shaped die. High-throughput laser drilling of the extruded body could follow, before or after loading of the payload and before or after cutting the extruded body to a specified length.

In another embodiment, another PGS casting method may be used to create the device body. The PGS casting method may employ an elastic tubular mold, such as a length of silicone tubing. Melted polymer may be loaded into the internal bore of the tubular mold, and a pin or wire may be inserted through the melted polymer. The pin or wire may have a head of larger cross-sectional area than the cross-section of the bore. The pin or wire may be inserted through the bore until the head is inside the tubular mold. The tubular mold may then stretch about the head to maintain the pin in position. On an opposite end of the tubular mold, a washer-type component having a hole for receiving the pin or wire may be slid along the pin or wire toward the tubular mold. The tubular mold may be stretched to cover the washer-type component, such that the melted polymer fills the inner space of the tubing. Additional grips may be used to prevent accidental slipping or loosening.

Once cast, the device body may be removed from the tubular mold by cutting the tubular mold along its length. The geometry of the device body may be determined by the inner diameter of the tubular mold and the diameter of the pin or wire. The device body may then be loaded and plugged as described above.

The devices and methods described above will be further understood with reference to the following non-limiting examples.

EXAMPLE 1

Making a Drug Delivery Device

Figure 9:
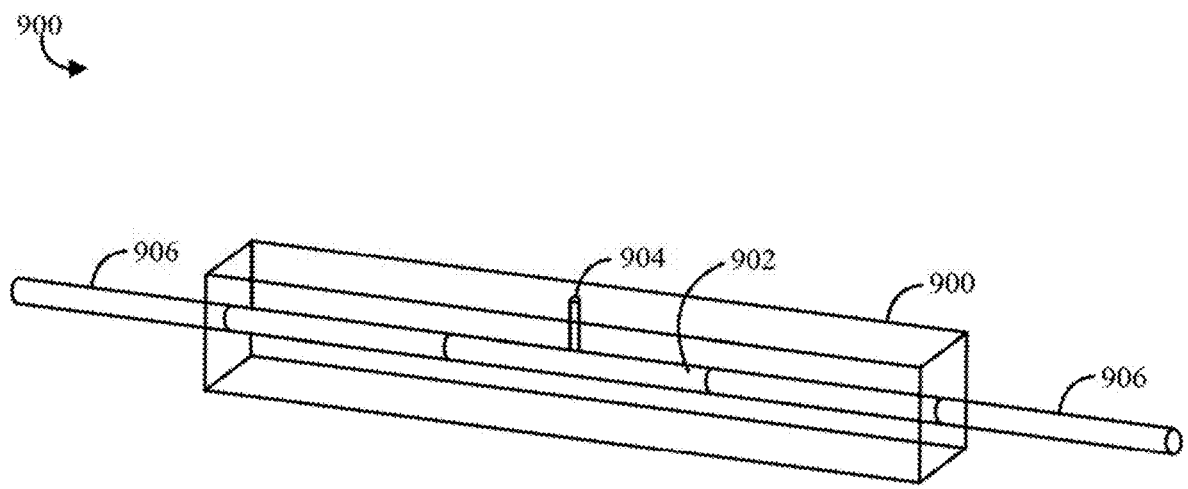
FIG. 9 is a schematic perspective view of a prototype drug delivery device tested in vitro.

A prototype PGS module for in vitro development was constructed and tested for drug release kinetics with ciprofloxacin, a fluoroquinolone commonly prescribed for chronic prostatitis and other UTIs. The prototype module 900 is shown in FIG. 9. The prototype module 900 was rectangular in shape with an internal cylindrical core for housing a 300 μm diameter drug rod 902 and contained a single 100 μm release orifice 904. Modules were formed through melting of PGS pre-polymer within a wire-strung aluminum mold followed by a polymerization reaction under heat and vacuum for 48 hours. The PGS casting remained within the mold as a laser microablation process drilled orifices at select locations on the top surface of the casting, which projected down to the embedded 300 μm diameter longitudinal wires.

Wires were pulled out of the mold through the sides and the PGS casting was removed from the mold and cut into rectangular modules measuring 10 mm×1.5 mm×1.5 mm, each with a single release orifice located in the module mid-section. The single release orifice was produced by laser machining.

The cast and cut PGS modules 900 were loaded with drug by inserting solid-packed ciprofloxacin rods 902 into the hollow bore of the PGS modules 900 (i.e., the device body). Then, the bore was plugged with stainless steel wire 906 to seal the drug 902 inside the PGS device body 900.

EXAMPLE 2

In Vitro Release Kinetics of the Drug Delivery Device

For in vitro measurement of release kinetics, prototype PGS devices loaded with ciprofloxacin were made as described in Example 1, were mounted on the inside of a glass vial, and were immersed in 2 mL de-ionized water. Time point measurements of ciprofloxacin-HCl (CIP) concentration in the surrounding media were taken roughly every 12 hours over an 8-10 day period using a quantitative HPLC-UV detection method developed for CIP.

Figure 10:
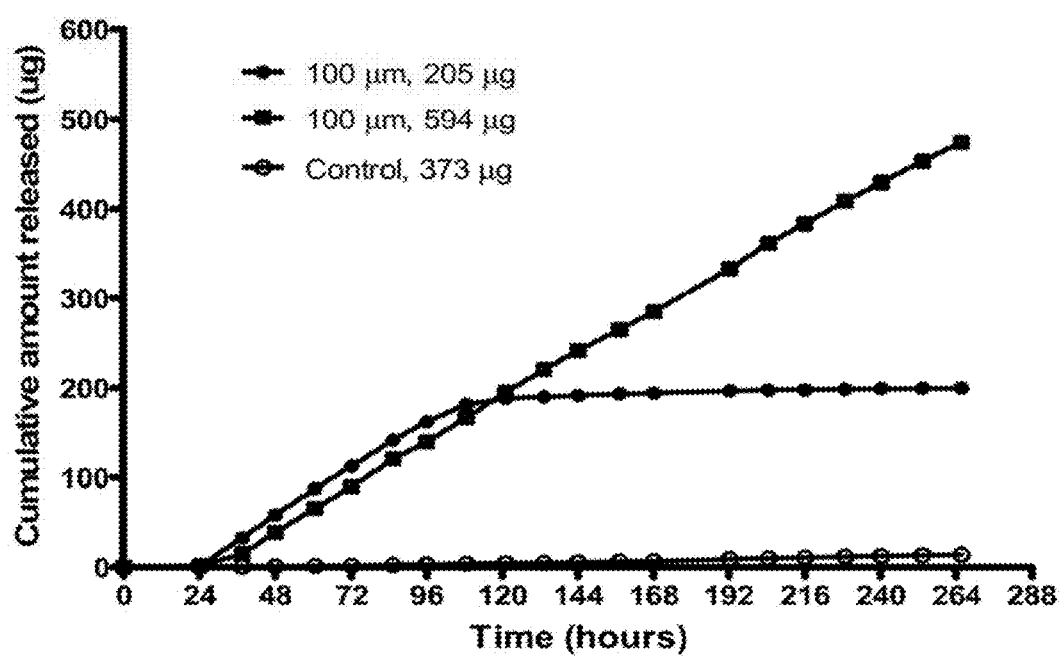
FIG. 10 is a graph demonstrating an experimental drug release profile for an in vitro experiment performed with a PGS module having a 100 μm orifice.

FIG. 10 illustrates the results of a representative CIP release experiment for two PGS modules having a 100 μm orifice and a control module without an orifice. The payload for each module is noted in μg. An induction time was observed before the onset of zero-order controlled release kinetics during which time water permeated into the devices and began to dissolve some of the drug payload. The two modules having 100 μm orifices were observed to release CIP at nearly the same rate after induction even though one of the modules contained nearly three times the payload of the other. As shown, the release profile of the 100 μm module having the smaller payload began to flatten once its CIP contents become fully dissolved and subsequently depleted. Diffusion of CIP through the PGS wall was not significant, as indicated by the results for the control module, which lacked a release orifice.

Figure 11:
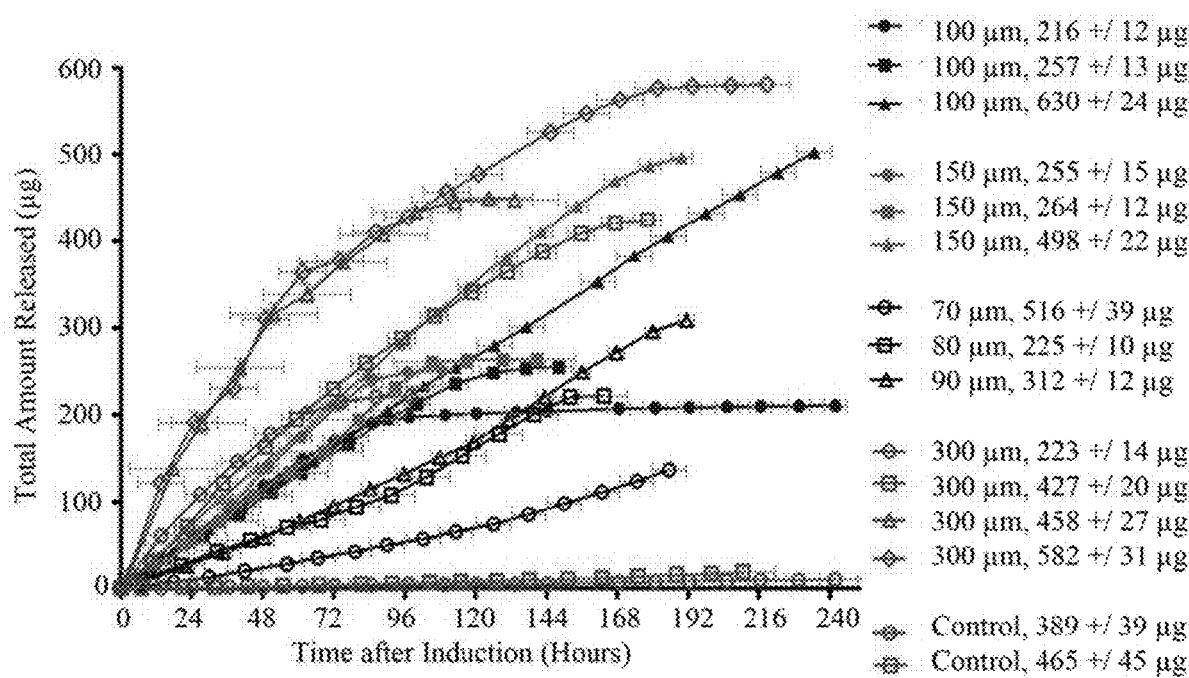
FIG. 11 is a graph of tabulated drug release results for orifices of various sizes.
Figure 12:
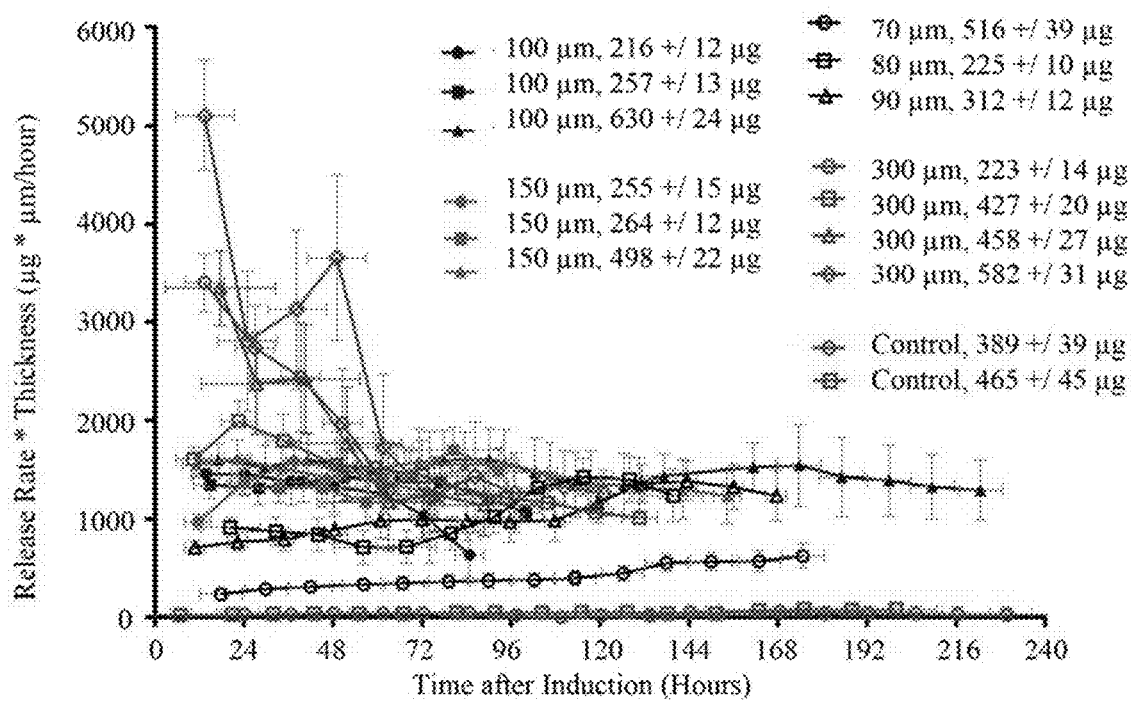
FIG. 12 is a graph of the tabulated drug release results for orifices of various sizes as shown in FIG. 11, corrected for variations in module thickness.

The experiment was repeated for a number of modules having release orifices of different sizes and initial drug payloads of different masses. FIGS. 11 and 12 illustrate the results of these experiments. For each module, orifice diameter is noted in μm and initial drug payload is noted in μg. FIG. 11 illustrates the actual release profile for each module, from an initial time point, which corresponds to onset of drug release after an induction period, to an end time point, which corresponds to a release of 90% of the total drug payload. FIG. 12 illustrates the same release profiles standardized or corrected for variations in wall thickness along the module. Particularly, the release profiles were multiplied by the average PGS wall thickness measured for the corresponding module.

As shown in FIG. 11 and FIG. 12, the PGS modules having 100 and 150 μm orifices demonstrated zero-order release of CIP due to osmotic pressure. As shown in FIG. 11, release from these modules demonstrated a relatively linear relationship with respect to time for most of the drug mass released from each module. The release rate for these modules remained roughly constant over time during release of up to 90% of the drug payload, as shown in FIG. 12. The release rate then decreased as the payload becomes fully dissolved, as seen in the leveling of the profiles in FIG. 11 as the devices approached completion of their payload release. The release rate for the modules with 100 and 150 μm orifices was relatively independent of initial payload for most of the drug mass released, as the release rates for different module were roughly the same even though some modules had 2-3 times the payload of others.

The release rate from modules have 300 μm orifices appeared to be dependent on payload, as initial release rates varied among modules having different drug payloads. The shapes of the release rate profiles for most of the modules having 300 μm orifices, with the possible exception of the module having the 427 μg payload, suggest that the drug was released due to a combination of osmotic and diffusion release mechanisms, as these release profiles appear significantly less linear than the release profiles for devices having 100 μm and 150 μm orifices. As shown in FIG. 12, the release rate for modules having 300 μm orifices declined over time during the majority of the payload release, suggesting that devices having 300 μm orifices do not permit osmotic control for zero-order release kinetics by allowing payload-dependent diffusion processes to occur.

FIG. 11 also suggests that modules having 150 μm orifices release CIP at a slightly faster rate than modules having 100 μm orifices. The thickness (h) of a semi-permeable membrane is noted to have a direct inverse relationship to drug release rate, as noted by osmotic pump theory in EQ. 1.

$$\text{Drug release rate} = \frac{dM}{dt} = \frac{A}{h}k\pi C \qquad \text{EQ. 1}$$

where A=wall surface area, h=wall thickness, k=produce of mechanical permeability and reflection coefficient, π=osmotic pressure at saturation, and C=drug solubility Wall thicknesses were measured for each module and were noted to be thinner for those modules having 100 and 150 μm orifices that expressed faster release rates. FIG. 12 accounts for this variability, as the release profile for each module was multiplied by the average of its measured wall thicknesses. Modules with 150 μm orifices were shown to release CIP at a comparable rate to modules with 100 μm orifices. Modules with orifices in the range of 70-90 μm demonstrated slower release rates than modules with 100 μm orifices, particularly in the case of modules with 70 μm orifices.

Thus, for modules having orifice sizes in the range of 70-90 μm, release rate was not independent of orifice size and was no longer under the exclusive control of osmotic parameters—the orifice was too small to allow hydrostatic pressure relief and proper osmotic release function. For modules having orifices in the range of 100 μm and 150 μm, release rate was independent of orifice size and was controlled by the thickness and surface area of the semi-permeable polymer wall, the osmotic pressure of the drug core and the solubility of the drug in accordance with osmotic pump drug release theory (EQ. 1). For modules having orifices in the 300 μm range, the orifice was too large to inhibit bulk diffusion effects, resulting in increased release.

The average measured release rate of CIP from a device having an orifice in the 100-150 μm range was 2.5±0.4 μg/hr in an in vitro de-ionized water environment. This release rate could be increased by adding multiple orifices with separated drug compartments, while the release duration could be prolonged by increasing the payload through the device length as needed for the requirements of the device therapy.

The dimensions of the device can be reduced to fit lengthwise within the core of a 14 or higher gauge needle or to fold in half to fit within a 16 Fr catheter. The osmotic pressure of the drug core can be increased by co-formulation with an agent of higher osmotic activity, such as sodium chloride, thus overcoming possible isotonic or hypertonic effects of an in vivo environment.

EXAMPLE 3

Delivery of Lidocaine to the Vesicular Gland of Rabbit

Figure 13:
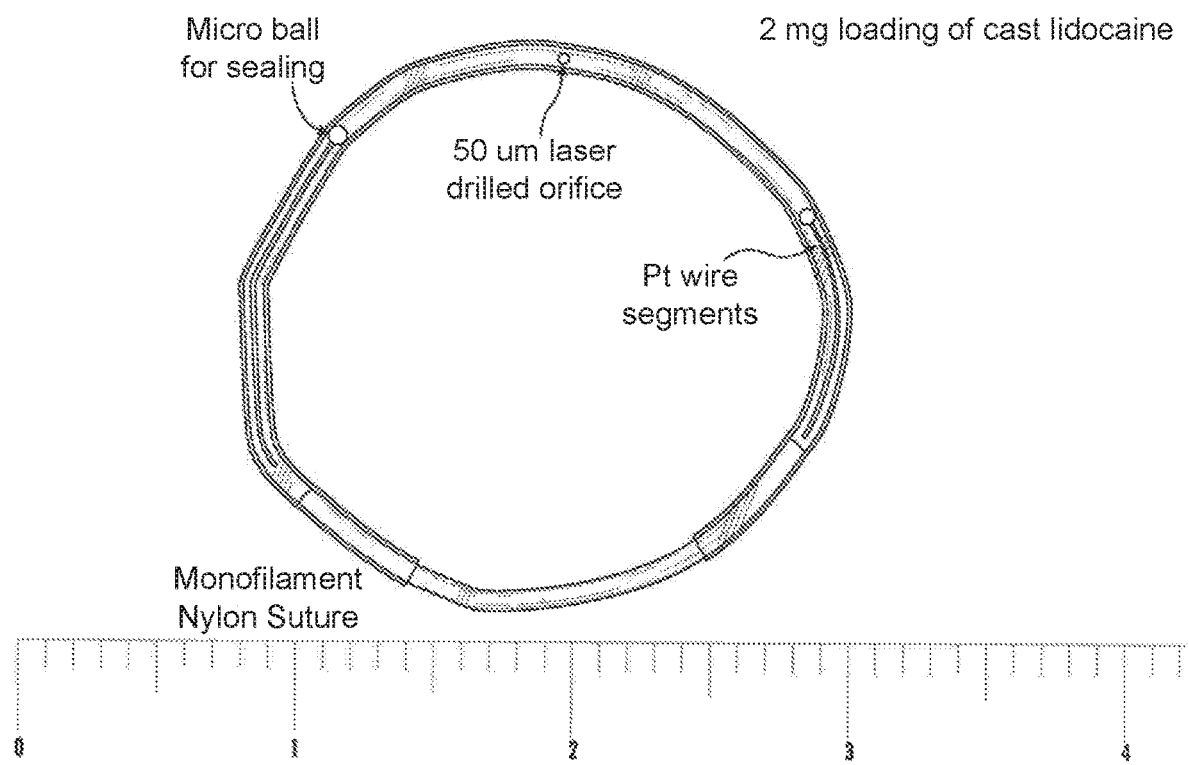
FIG. 13 illustrates a non-resorbable device used in an experiment conducted in vivo in rabbit.
Figure 14:
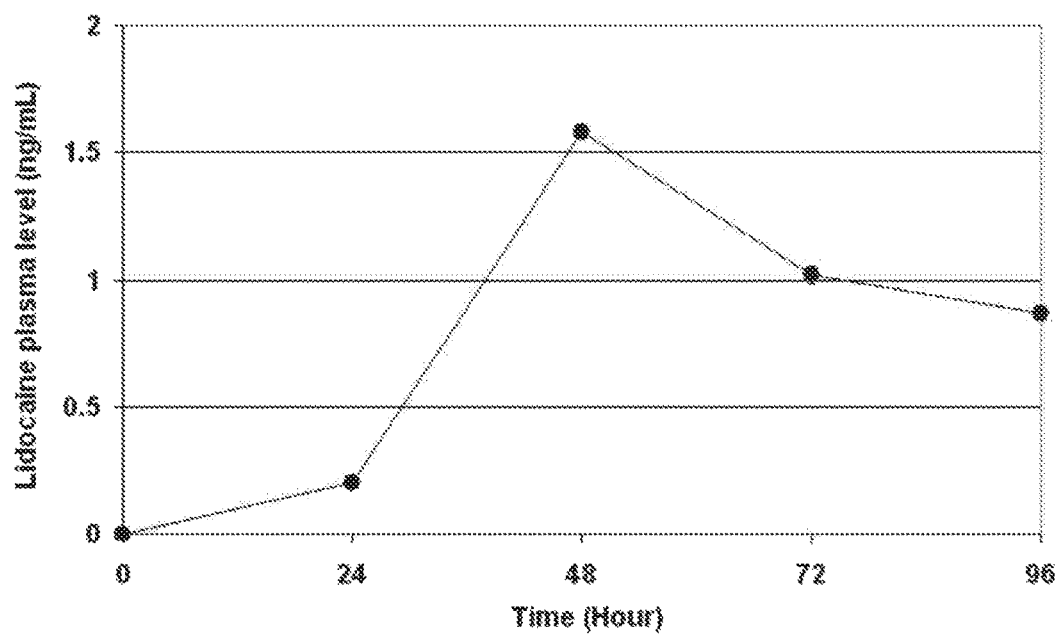
FIG. 14 is a graph illustrating lidocaine plasma concentration over time for the experiment conducted in vivo in rabbit.

A pilot in vivo experiment was conducted with a non-resorbable silicone device implanted in the vesicular gland of a rabbit (2.7 kg, New Zealand White, male). The drug used was lidocaine and total loading was 2 mg. This experiment was designed to simulate the situation when the device is implanted in a location other than the bladder, such as the seminal vesicle for men. The non-resorbable device for a rabbit experiment is shown in FIG. 13, and lidocaine plasma concentration over the time is shown in FIG. 14.

EXAMPLE 4

Method of Forming a Drug Delivery Device Body

A casting method was used to make a device body having a length of about 7.62 cm, a hollow reservoir having a diameter of about 330 µm, a first orifice located about 2.81 cm from a first end of the device, and a second orifice located about 2.81 cm from a second end of the device. The orifices had a diameter of about 100 µm. Such a device was formed by casting PGS in a mold with embedded steel wires. The mold had a length of about 7.62 cm. A number of steel wires were strung through the mold along its length. Each wire had a diameter of about 330 µm. After the PGS was cast, orifices were laser drilled into the device bodies. The PGS was removed from the mold and cut into individual device bodies.

In another example, a mold was provided for forming a number of device bodies. The mold was an aluminum mold, and a PGS pre-polymer was placed therein. Wires were inserted into the mold for forming the payload reservoirs. The mold had a length of about 150 mm and the wires were made of stainless steel. After baking, the cross-linked PGS was removed from the mold, cut into sections, and further processed to yield a number of device bodies. Sealing balls were inserted to plug one end of each payload reservoir, with the other end being left open to form the release orifice.

EXAMPLE 5

Method of Making a Drug Rod and Associated Drug Delivery Device

A method of making a drug rod and associating the drug rod with a delivery device body, or housing, was tested.

The drug rod was cast using solid powder within a die. The die was formed from silicone to facilitate expulsion of the packed drug rod and to maintain a sterile and transparent environment. A hole having a diameter of about 300 µm was formed through the die. The die was mounted on an aluminum base with an embedded wire, which penetrated the hole of the silicone die. The embedded wire (diameter of about 340 µm) penetrated the silicone casting to a height of about 3 mm. The CIP powder was deposited on top of the silicone die and packed into the core of the die using a steel wire (diameter of about 300 µm) secured within a wire gauge drill chuck. The compressed CIP expanded the diameter of the die core, forming a depot during the packing procedure. Upon exiting the die, the drug rod had a diameter of about 300 µm and a length of about 1 mm to about 22 mm. The drug rod remained attached to the end of the packing wire, allowing for positioning the drug rod in the core of a PGS module held open by reverse clamped tweezers.

The drug rod was positioned in a drug delivery device. Specifically, a CIP drug rod was be positioned in a PGS device. The PGS device had a length of about 1 cm, and the CIP drug rod had a length of about 3-5 mm and a width of about 400-550 µm. The orifice had a diameter of about 103 µm. The drug loaded housings was sealed with steel wire plugs.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable medical device comprising:
a resorbable, elastic device body having a first closed end, an opposed second closed end, at least one elongated sidewall extending between the first and second closed ends, and at least one payload reservoir defined thereby; and
a payload stored in the payload reservoir,
wherein the device body provides controlled release of the payload in vivo by diffusion through the sidewall of the device body, and
wherein the implantable medical device is dimensioned and has an elasticity suitable for deployment of the medical device into a patient's bladder via the patient's urethra.

2. The device of claim 1, wherein the device is deformable from a first configuration suited for passing the medical device through a lumen of a urethral catheter or cystoscope into the patient's bladder to a second configuration suited for retaining the device in the bladder upon exiting the urethral catheter or cystoscope.

3. The device of claim 1, wherein the resorbable, elastic device body comprises an elastomeric polymer.

4. The device of claim 3, wherein the elastomeric polymer is a hydrophobic elastomeric polyester.

5. The device of claim 4, wherein the hydrophobic elastomeric polyester is a poly(glycerol-sebacic acid).

6. The device of claim 3, wherein the elastomeric polymer comprises a poly(caprolactone), a polyanhydride, an amino alcohol-based poly(ester amide), or a poly(octane-diol citrate).

7. The device of claim 1, wherein the payload comprises a drug.

8. The device of claim 7, wherein the drug comprises an antibiotic agent, an immunosuppressant, an anti-inflammatory agent, a chemotherapeutic agent, or an anesthetic agent.

9. The device of claim 7, wherein the payload is in a solid or semi-solid form.

10. The device of claim 1, wherein the body comprises an elastic retention frame comprising a hoop, coil, or spiral shape configured to retain the device in the patient.

11. An implantable drug delivery device comprising:
a device body formed from a resorbable elastomeric polymer, the device body having an elongated annular sidewall defining a hollow bore; and
a payload consisting essentially of solid or semisolid drug loaded into the hollow bore,
wherein the device is deformable from a first configuration suited for passing the drug delivery device through a lumen of a urethral catheter or cystoscope into a patient's bladder to a second configuration suited for retaining the device in the bladder upon exiting the urethral catheter or cystoscope.

12. The device of claim 11, wherein the resorbable elastomeric polymer comprises a hydrophobic elastomeric polyester which degrades in vivo by surface erosion.

13. The device of claim 11, wherein the hydrophobic elastomeric polyester is a poly(glycerol-sebacic acid).

14. The device of claim 11, wherein the body comprises an elastic retention frame comprising a hoop, coil, or spiral shape configured to retain the device in the patient.

15. The device of claim 1, wherein the payload consists essentially of a drug.

* * * * *